United States Patent [19]

Parker

[11] Patent Number: 5,339,805

[45] Date of Patent: * Aug. 23, 1994

[54] BLIND OROLARYNGEAL AND OROESOPHAGEAL GUIDING AND AIMING DEVICE

[76] Inventor: Jeffrey D. Parker, 2219 Grandin Rd., Cincinnati, Ohio 45208

[ * ] Notice: The portion of the term of this patent subsequent to Aug. 13, 2008 has been disclaimed.

[21] Appl. No.: 995,965

[22] Filed: Dec. 23, 1992

Related U.S. Application Data

[63] Continuation of Ser. No. 879,873, May 7, 1992, Pat. No. 5,174,283, which is a continuation-in-part of Ser. No. 433,687, Nov. 8, 1989, Pat. No. 5,038,766.

[51] Int. Cl.$^5$ ............................................. A61M 16/00
[52] U.S. Cl. ................... 128/200.26; 128/10; 128/207.14
[58] Field of Search .................... 128/4, 10, 11, 15, 16, 128/200.26, 200.24, 207.14, 207.15, 911, 912

[56] References Cited

U.S. PATENT DOCUMENTS

| | | | |
|---|---|---|---|
| 3,754,554 | 8/1973 | Felbarg | 128/200.26 |
| 3,756,244 | 9/1973 | Kinnear et al. | 128/207.14 |
| 3,802,440 | 4/1974 | Salem et al. | 128/200.26 |
| 3,874,377 | 4/1975 | Davidson | 128/207.15 |
| 3,908,665 | 9/1975 | Moses | 128/207.14 |
| 3,930,507 | 1/1976 | Berman | 128/207.14 |
| 3,948,255 | 4/1976 | Davidson | 128/207.14 |
| 4,068,658 | 1/1978 | Berman | 128/200.26 |
| 4,155,365 | 5/1979 | Boslau | 128/207.15 |
| 4,166,468 | 9/1979 | Haynie | 128/207.15 |
| 4,167,946 | 9/1979 | Sandstrom | 128/207.17 |
| 4,211,234 | 7/1980 | Fisher | 128/200.26 |
| 4,231,365 | 11/1980 | Scarberry | 128/207.15 |
| 4,256,099 | 3/1981 | Dryden | 128/200.26 |
| 4,338,930 | 7/1982 | Williams | 128/200.26 |
| 4,365,625 | 12/1982 | Rind | 128/207.14 |
| 4,497,318 | 2/1985 | Donmicheal | 128/202.28 |
| 4,509,514 | 4/1985 | Brain | 128/207.15 |
| 4,612,927 | 9/1986 | Krüger | 128/200.26 |
| 4,655,214 | 4/1987 | Lindner | 128/207.18 |
| 4,672,960 | 6/1987 | Frankel | 128/200.26 |
| 4,683,879 | 8/1987 | Williams | 128/200.26 |
| 4,685,457 | 8/1987 | Donenfeld | 128/207.14 |
| 4,773,394 | 9/1988 | Reichstein et al. | 128/4 |
| 4,825,858 | 5/1989 | Frankel | 128/200.26 |
| 4,832,020 | 5/1989 | Augustine | 128/207.14 |
| 4,840,172 | 6/1989 | Augustine et al. | 128/207.14 |
| 4,919,126 | 4/1990 | Baildon | 128/207.14 |
| 5,038,766 | 8/1991 | Parker | 128/200.26 |
| 5,042,469 | 8/1991 | Augustine | 128/200.26 |
| 5,174,283 | 12/1992 | Parker | 128/200.26 |
| 5,203,320 | 4/1993 | Augustine | 128/10 |

FOREIGN PATENT DOCUMENTS 228898 of 0000 Argentina .

(List continued on next page.)

OTHER PUBLICATIONS

Liban, J. B. et al., *A New Blade for Blind Endotracheal Intubation*, British Journal of Anesthesia, vol. 49, pp. 1279–1280.

(List continued on next page.)

*Primary Examiner*—Edgar S. Burr
*Assistant Examiner*—Eric P. Raciti
*Attorney, Agent, or Firm*—Wood, Herron & Evans

[57] ABSTRACT

To facilitate rapid, accurate, blind access to the larynx or esophagus such as for emergency intubation of a patient's trachea and suctioning of the hypopharynx or esophagus, a medical device (10) includes an anatomically contoured guide element (12) having a channel (22) therethrough. Guide element (12) is positioned about and atop the larynx such that the wall of the channel forms an upward continuation of the laryngeal wall. An orotracheal tube (18) advanced through the channel is guided exclusively into the larynx and trachea without substantial risk of accidental intubation of the esophagus or other areas of the hypopharynx. Tunnels (150, 160) may be provided through the guide element for blindly guiding or aiming other tubular-type members selectively into the esophagus or larynx. A tubular handle (14) or curved blade (454) is connected to the guide element (12) to blindly insert guide element (12) into the throat. Alternative embodiments (310, 350, 410, 450) of medical device (10) are also described.

20 Claims, 13 Drawing Sheets

FOREIGN PATENT DOCUMENTS

| | | |
|---|---|---|
| 233761 | 8/1987 | European Pat. Off. . |
| 234847 | 9/1987 | European Pat. Off. . |
| 2489686 | 9/1981 | France . |
| 1535060 | 12/1978 | United Kingdom . |
| 2137096 | 10/1984 | United Kingdom . |
| 2205499 | 12/1988 | United Kingdom . |
| 2229367 | 9/1990 | United Kingdom . |

OTHER PUBLICATIONS

J. M. Bleyer, Some Practical Hints in Connection with Intubation of the Larynx, N. Y. Med. Jour., p. 122 (Feb. 2, 1889).

J. M. Bleyer, Tongue and Larynx Tractor for the Performance of Forced Laryngoscopy in Children, Archives of Pediatrics, pp. 597–599 (Oct. 1988).

Leroy, Recherches Sur L'Asphyxie, 7 J. de Physiologigue, 45 65, 1827.

Knapp, Medical Record, N.Y., 322, Aug. 29, 1986.

Understanding Anasthesia Equipment, pp. 342–343 and 346–349.

Fundamentals of Tracheal Intubation, pp. 74–76 and FIGS. 4–9 at p. 56.

Machida Nasopharyngo–Laryngoscope.

Anasthesiology Review, p. 24, vol. VIII, No. 1.

Rusch Super Safety Clear Endotracheal Tubes.

"British Journal of Anaesthia" The Laryngeal Mask–A New Concept in Airway Management; 1983; vol. 55; pp. 801–805.

"Anasthesia"; Three Cases of Difficult Intubation Overcome By The Laryngeal Mask Airway; 1985; vol. 40; pp. 353–355.

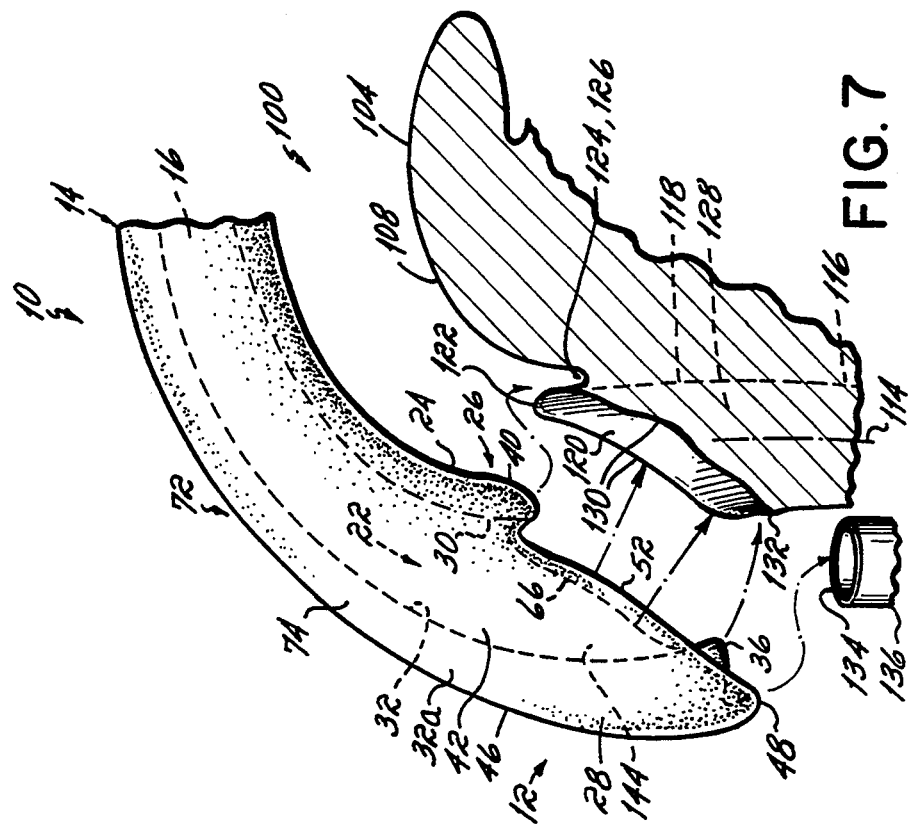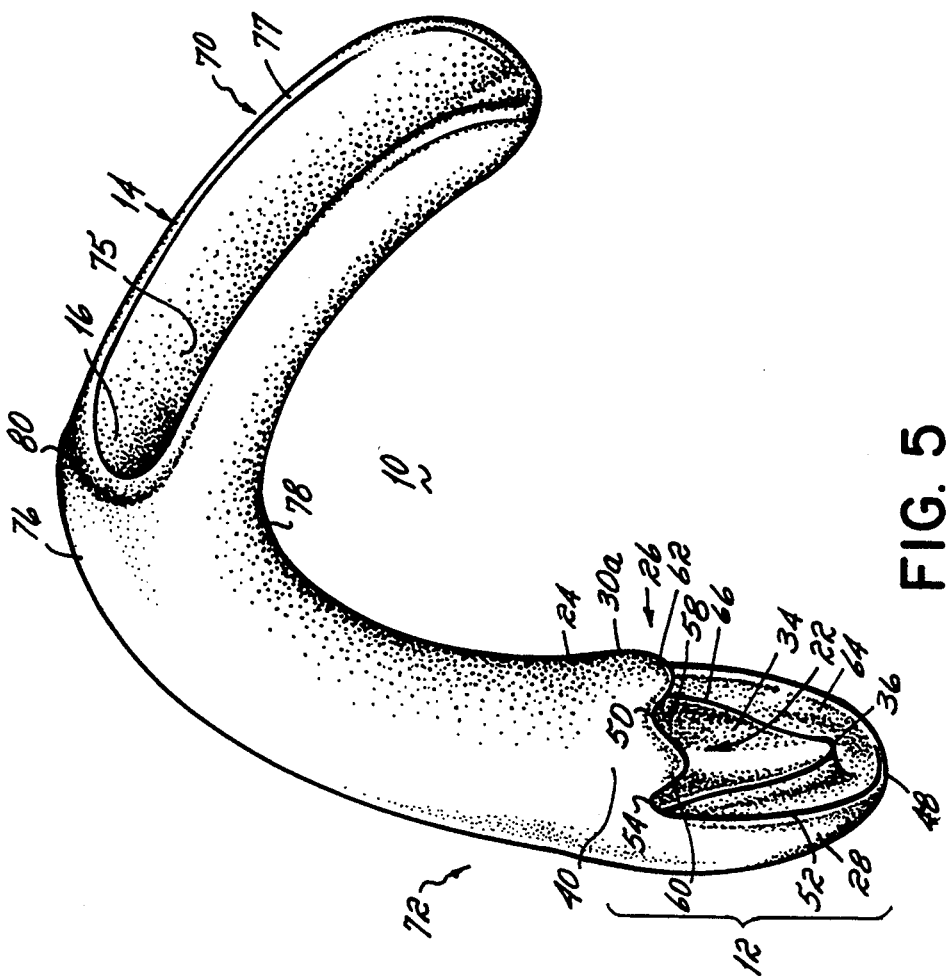

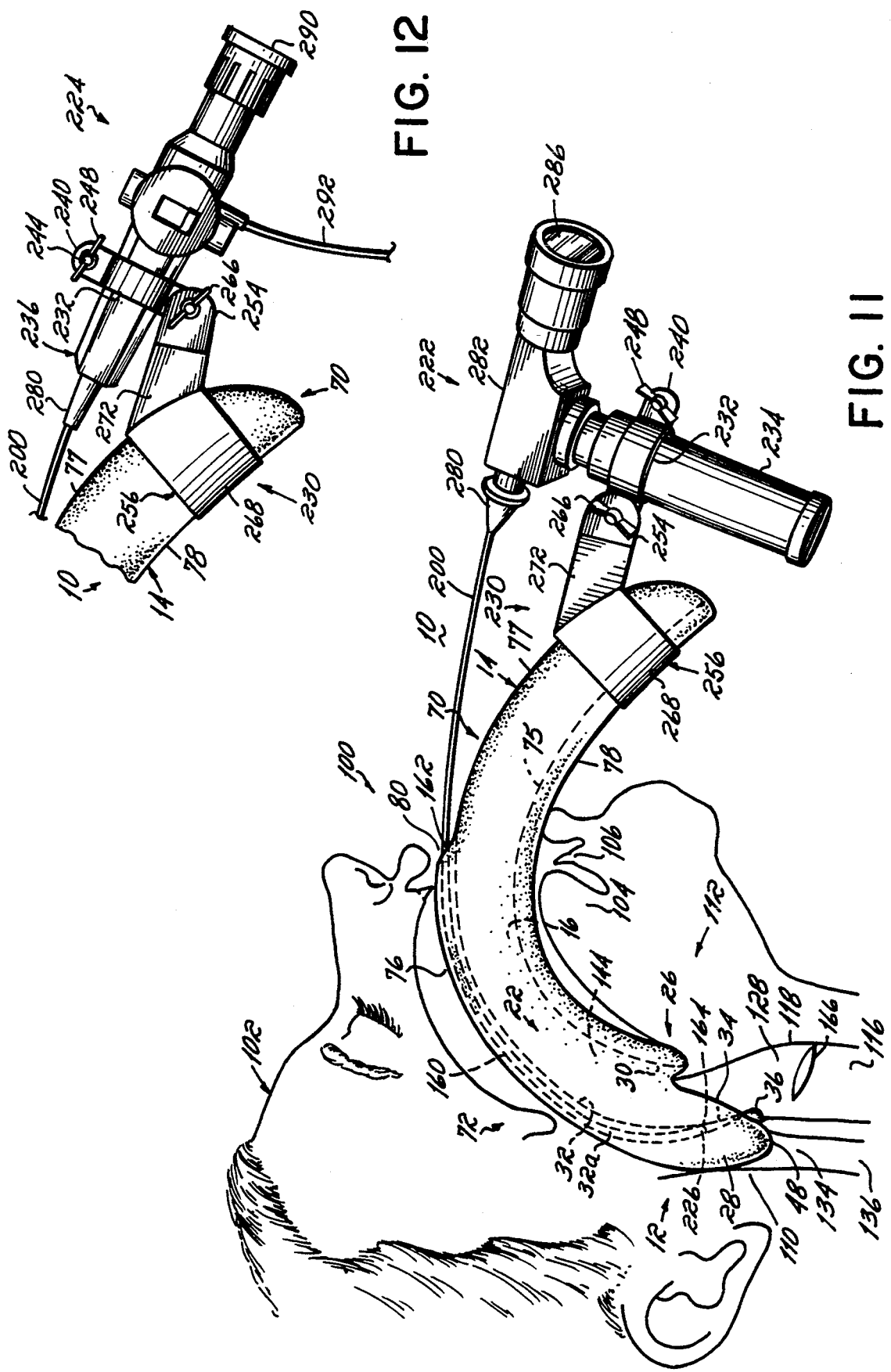

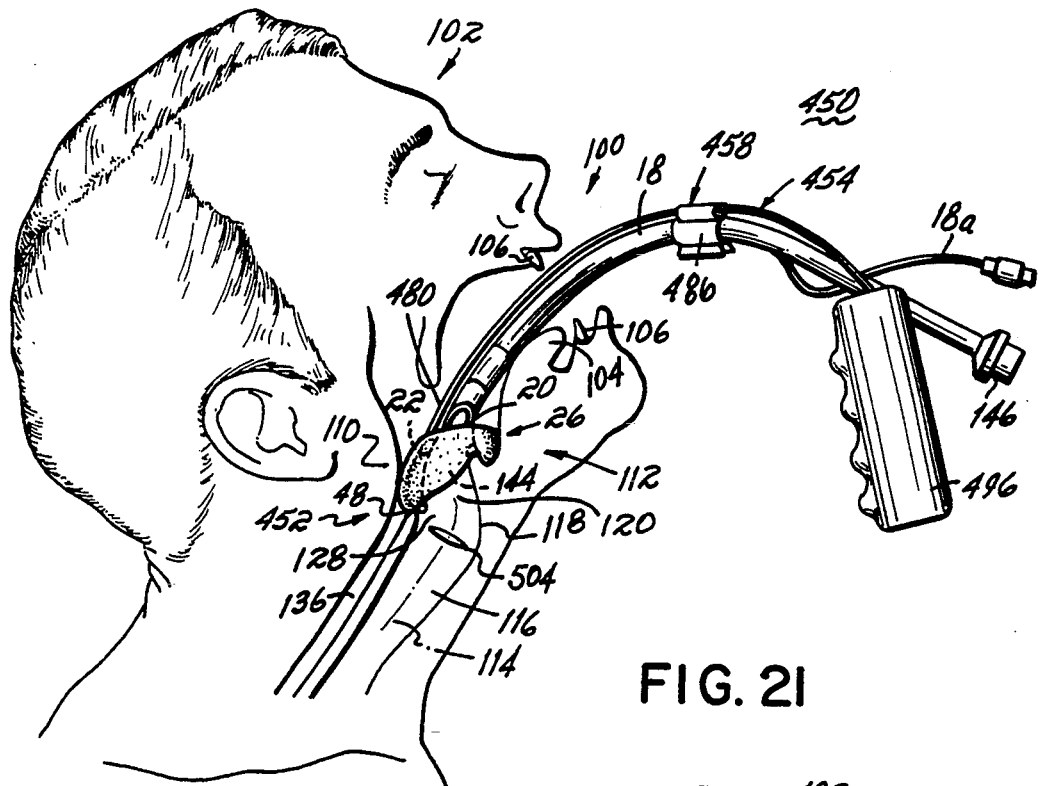
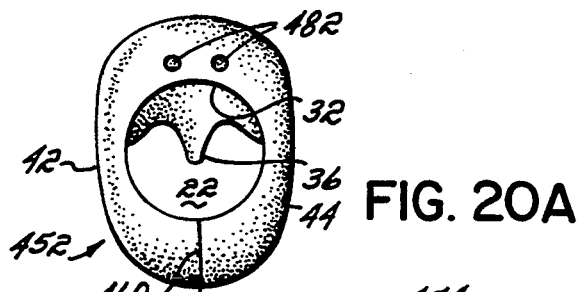
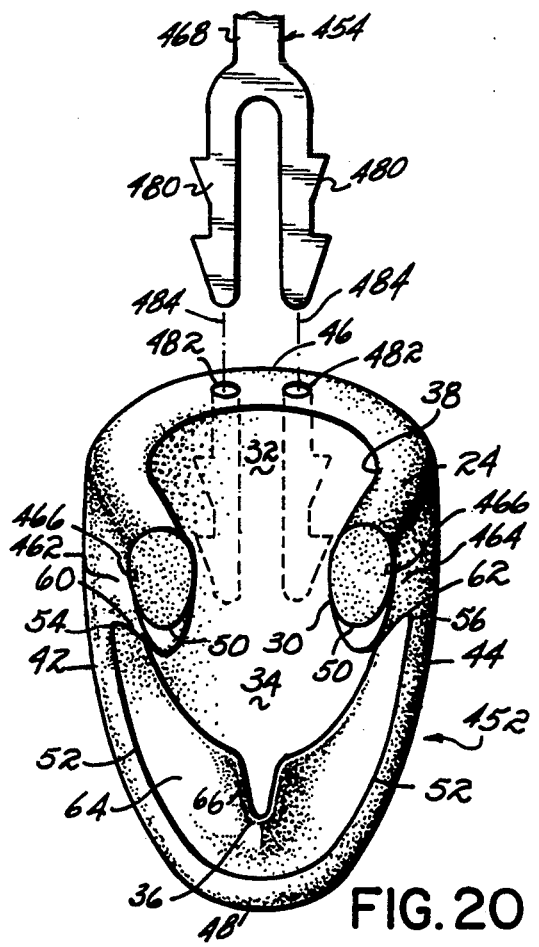
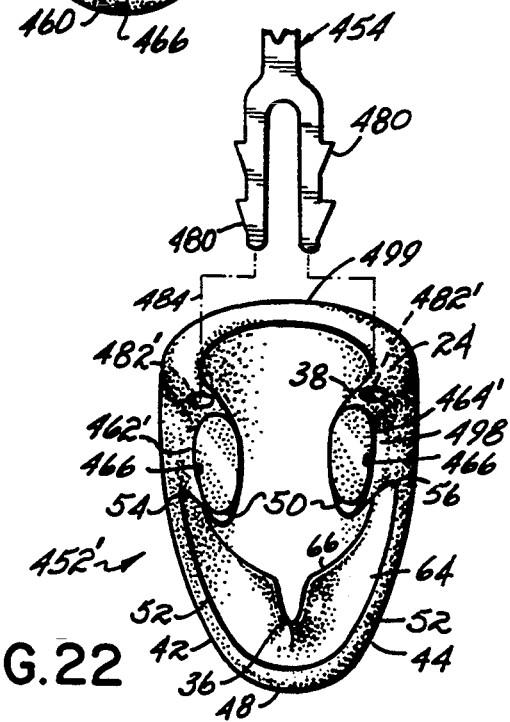
FIG. 21
FIG. 20A
FIG. 20  FIG. 22

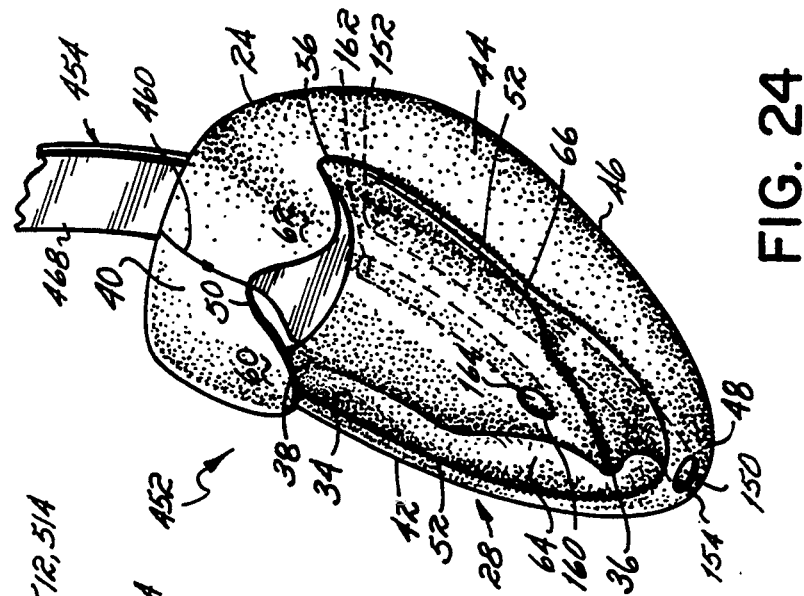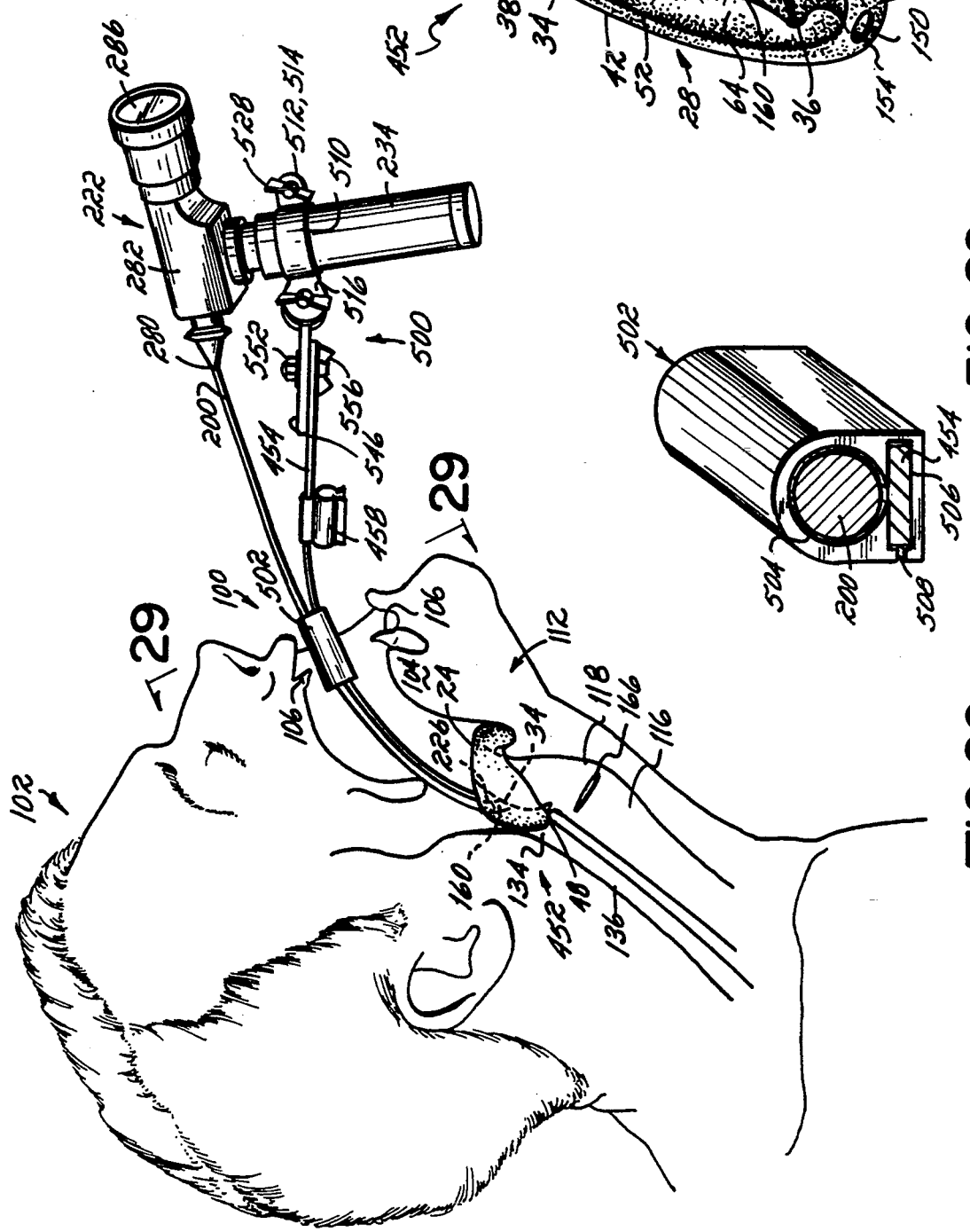

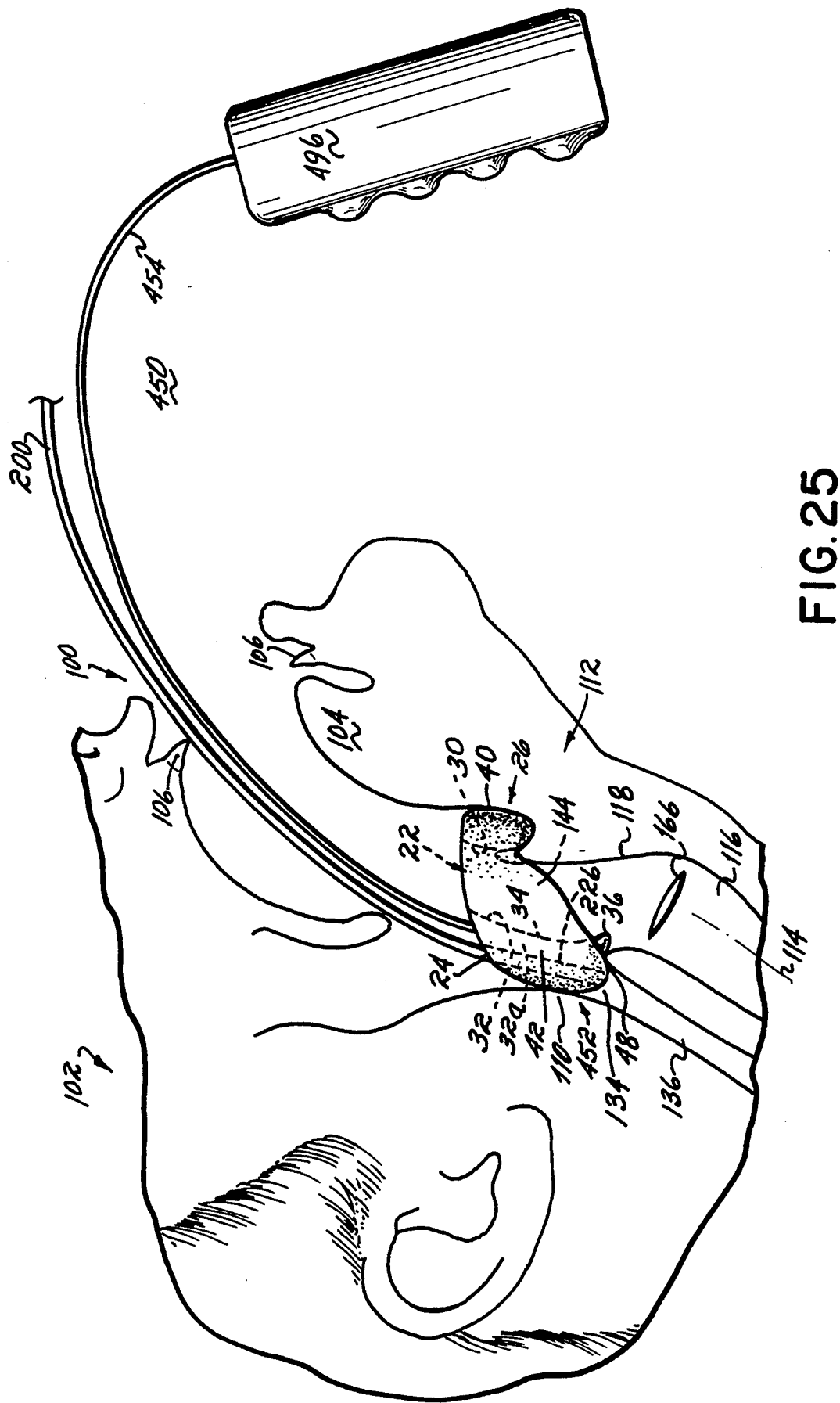

BLIND OROLARYNGEAL AND OROESOPHAGEAL GUIDING AND AIMING DEVICE

RELATED APPLICATION

This application is a continuation of my U.S. patent application Ser. No. 07/879,873, filed May. 7, 1992 now U.S. Pat. No. 5,174,283, which is a continuation of PCT international application Serial No. PCT/US90/06351 filed Oct. 31, 1990 which is a continuation-in-part of my United States patent application Ser. No. 07/433,687 filed Nov. 8, 1989, now U.S. Pat. No. 5,038,766 the disclosures of which are incorporated herein by reference.

BACKGROUND OF THE INVENTION

I. Field of the Invention

The present invention relates to a medical device which blindly and selectively facilitates the rapid, gentle and accurate guiding, aiming, and stabilizing of tubular or elongated members relative to the larynx and esophagus of humans and animals, especially under emergency conditions. The present invention further relates to such a device to facilitate rapid, gentle, blind oral intubation of the larynx or esophagus for purposes of ventilation, suctioning, inspection with a fiberoptic endoscope, forceps retrieval of foreign bodies, or remote biopsy, as desired.

II. Description of the Prior Art

As is well known, breathing and swallowing are accomplished through respective canals which open at the back of throat (the pharynx). One such canal extends through the larynx and trachea to the lungs to allow breathing. The other canal extends through the esophagus to the stomach for passage of food. The openings to the larynx and esophagus are positioned very close together. That positioning, along with other closely adjacent anatomical spaces at the back of the throat, presents difficulties to a medical provider needing to obtain rapid, specific access to a selected one of the canals, particularly in emergency situations.

For example, when a patient stops breathing, it is imperative that effective ventilation be instituted as soon as possible. Ventilation is best accomplished by forcing air through an orotracheal tube inserted through the mouth and laryngeal opening and into the trachea. Current methods of orotracheal intubation, the process of inserting the tube, are frequently slow and difficult, and prone to life-threatening error. The considerable angle between the axes of the mouth and larynx, and the intervening presence of the tongue and epiglottis, make it impossible to see the larynx through the mouth without special positioning and instrumentation. Also, there is ample space around the larynx into which an orotracheal tube can be easily and unwittingly misdirected. Indeed, it is not uncommon for the tube to be accidently inserted into anatomical spaces surrounding the larynx, such as the closely adjacent esophagus, rather than the larynx. Similarly, it is sometimes necessary to introduce a suction catheter at or into the esophageal opening to evacuate vomitus from the throat prior to orotracheal intubation. But, such a catheter can be accidently inserted into the larynx and trachea instead.

Whether ventilation of the lungs or suctioning along the oroesophageal axis is desired, prior art devices and methods do not assure the exclusive passage of the tubular member into the intended orifice (of the larynx or esophagus). The major danger is that if the tubular member is incorrectly placed, attempts to ventilate or suction the patient may instead result in suffocation. In a non-breathing patient, for example, if ventilation is supplied to the stomach rather than to the lungs through an orotracheal tube which has been accidentally introduced into the esophagus instead of the trachea, the stomach will inflate while the lungs receive no air and the patient will suffocate. Similarly, if suction is applied to a catheter which has been accidentally introduced into the trachea instead of the esophagus, the air in the trachea and lungs will be evacuated and the patient will suffocate. Thus, there is a need for an accurate means to direct tubes rapidly and selectively into the intended openings of either the larynx or esophagus.

One known method of guiding an orotracheal tube involves inserting a finger into the patient's throat and, using the sensation of touch, guiding the orotracheal tube down into the laryngeal opening. This is a "blind" method, in that the medical provider does not see the larynx when placing the tube. However, this blind, tactile method of intubation is not favored, and often results in accidental intubation of the esophagus instead of the trachea, frequently with tragic consequences. An instrument-guided method of blind intubation was developed in France by Leroy in 1827. But Leroy's two-bladed intubation speculum lacked any means to prevent accidental intubation of the esophagus or other areas adjacent to the larynx.

In 1912, a non-blind method of orotracheal intubation was developed using a blade laryngoscope to expose the larynx and allow the intubationist to "see" where to insert the orotracheal tube. This non-blind (or "visual") laryngoscopic method of orotracheal intubation was quickly accepted by the medical community as a logical way to eliminate the errors and complications inherent in blind intubation, and has become the method of choice for orotracheal intubation in the emergency setting.

Unfortunately, laryngoscopic orotracheal intubation has not only failed to eliminate accidental misintubation, but has introduced its own set of serious limitations and complications, sometimes catastrophic. For example, blade laryngoscopes, the devices used most for emergency orotracheal intubation, nearly always require that the laryngoscopist be positioned above the head of the patient to be intubated, and that the patient be lying in a supine position with mouth opened widely and neck extended so as to straighten the oral-pharyngeal-laryngeal axis in order to permit a transoral view of the larynx so that a tube may be inserted thereinto. But such relative positioning of the patient and laryngoscopist is frequently unachievable, where for example, the patient is trapped in an awkward position such as inside a wrecked vehicle. Similarly, the patient's mouth may not be widely openable where, for example, the temporomandibular joint is ankylosed or the jaw is broken; and extending the patient's neck may cause or aggravate a cervical spine injury. Another problem with laryngoscopic intubation is that substantial force must be applied via the rigid blade of the laryngoscope to depress the tongue and pull the epiglottis forward far enough to obtain a view of the larynx. This force frequently results in teeth being broken by the laryngoscope blade, and occasionally results in bleeding in the throat. Such bleeding can be uncontrollable in patients with thrombocytopenia or other bleeding disorders, and can prevent an adequate view of the larynx, thus hindering the attempt to intubate. A further problem is that during laryngoscopic intubation, there is no satisfactory way to prevent vomitus from rising from the esophagus into the throat, where it can obscure a view of the larynx, impairing the attempt to intubate, and where it can also be aspirated into the trachea and lungs, causing aspiration pneumonia and impairing effective ventilation. The presence of substantial blood, vomitus, or other debris in the throat currently requires that a suction catheter be introduced into the throat to evacuate these larynx-obscuring substances. But pausing to suction the throat delays intubation, since the suction catheter itself frequently obscures the view through the laryngoscope and interferes with manipulation of the orotracheal tube in the throat. Thus, orotracheal intubation cannot proceed easily and safely until the suction catheter is removed from the throat—at which time, further bleeding or vomiting may necessitate its reintroduction.

Another problem is that the technique of laryngoscopic intubation requires considerable training, skill, and experience before a high rate of success can be expected. One or more assistants are frequently needed by the laryngoscopist to perform ancillary tasks such as holding the patient's neck in an extended position, pressing externally on the larynx, and suctioning the throat. A further problem is that metal laryngoscopes are relatively expensive to buy and maintain. Perhaps the greatest imperfection of blade laryngoscopes is that they do not assure accurate orotracheal intubation. Even the laryngoscopes which substitute long, flexible or malleable fiberoptic image guides for rigid blades have major disadvantages. For example, they are very expensive, fragile, difficult to learn to use, slow in actual use, frequently require the use of an assistant, and have no reliable way to rapidly achieve correct and stable orolaryngeal positioning of their distal tips. Several attempts have been made to supersede the laryngoscope with devices which purport to facilitate blind intubation. But these devices have never overcome the principal problem of Leroy's device and of blade laryngoscopes, in that they have provided no safe and effective means to assure accurate orotracheal intubation.

For example, the intubation device shown in U.S. Pat. No. 4,832,020 includes structure to abut the front of the epiglottis to prevent the device from being inserted too far into the throat. However, there is no assurance of accurate and stable alignment of that device with respect to the laryngeal opening to be sure the orotracheal tube will be properly guided into the larynx. Moreover, that device requires tension to be blindly applied to the tongue, hyoid bone, hyo-epiglottic ligament, and epiglottis to pull these structures forward in order to achieve exposure of the glottis sufficient for intubation to be performed. But, with that device, too little or too much force could be applied, resulting in misalignment or misintubation.

OBJECTS OF THE INVENTION

Thus, there is a need for a device for emergency orotracheal intubation which overcomes the above problems. Specifically, such a device should facilitate rapid orotracheal intubation of patients regardless of their position with respect to the intubationist, and without opening the mouth widely or extending the neck. The device should not require the application of substantial force within the mouth or throat. It should prevent or remove the accumulation of vomitus (or blood or mucus) in the throat during intubation. Alternatively, the device should facilitate blind orotracheal intubation which will not be hindered by the presence of larynx-obscuring vomitus, blood, or mucus. The device should be relatively inexpensive to buy and maintain, simple to use, easy to learn and teach, and equipped with safe and effective means to minimize the risk of misintubation. It should also be capable of rapidly and blindly aiming the forward tip of the fiberbundle of a fiberoptic laryngoscope into the larynx with a high degree of accuracy and stability so that emergency visual orotracheal intubation using such laryngoscopes will become feasible. It should also facilitate the rapid placement of other tubular or elongated members, such as grasping and biopsy forceps, into or adjacent the laryngeal or esophageal openings for examination or treatment of the patient.

SUMMARY OF THE INVENTION

The present invention provides for safe and rapid placement of a tubular or elongated member relative the desired anatomical opening at the back of the throat without the drawbacks encountered in the prior art. In its broadest sense, the present invention provides a guide element receivable through the mouth and into the back of the throat, the guide element having a channel wall extending longitudinally along a central portion of the guide element, the guide element further having anatomically contoured surfaces which cooperate with corresponding anatomical features (processes and recesses) at the back of the throat to stop rearward progress of the guide element as it is pushed into the throat and to center and stabilize the guide element in a relatively fixed position with respect to the larynx such that the channel wall of the guide element is substantially aligned and contiguous with at least the rear edge of the tubular wall of the laryngeal opening to define a substantially continuous upward extension of at least the posterior portion of the laryngeal wall along which a tube may be advanced directly into the larynx. The guide element is preferably comprised of a soft semiflexible material so as not to traumatize the throat.

Preferably, a recessed surface surrounds the lower end of the channel wall. The exterior of the laryngeal wall adjacent the rear and side edges of the laryngeal opening fits into the recess to further stabilize and align the channel wall.

Further preferably, the upper portion of the guide element is an annulus having a channel therethrough defined by the channel wall. The annulus portion may also be anatomically contoured to cooperate with anatomical features of and surrounding the larynx to help stabilize the guide element and position the channel thereof against the laryngeal opening such that the upward extension of the laryngeal wall defined by the channel wall constitutes a substantially exclusive airway path extension atop and coaxial the laryngeal lumen.

The upward extension of the laryngeal wall defined by the channel wall may function as a tube guideway along which a tubular or elongated member may be passed into or aimed at the laryngeal opening. The guide element may further be utilized to guide or aim such a member into the esophageal opening via a separate tunnel through the guide element. When so utilized, the laryngeal wall extension serves as an airway path to maintain breathability of the patient during esophageal intubation.

The present invention further contemplates provision of a handle member coupled to the guide element, the handle member preferably being curved to conform generally to the curvature between the mouth and the larynx, by which to insert the guide element through the patient's mouth and into the back of the throat such that the guide element may be moved within the throat by manipulation of the proximal end of the handle member outside the mouth. As the guide element approaches the back of the throat, the anatomical mating surfaces of the guide element cooperate with the anatomical features at the back of the throat to achieve the desired alignment. As a consequence, the guide element may be blindly yet properly positioned in the patient's throat.

Preferably, the handle member is tubular and includes a lumen therethrough with the wall of the lumen being continuous with the guide element channel wall and serving to extend the guide element channel wall upward through and beyond the mouth so that an orotracheal tube inserted from outside the mouth through the lumen of the handle member will pass into and through the guide element for intubation. The lumen through the handle also permits the guide element to be removed after the tube is placed into the larynx by slidably retracting the handle member and guide element up over and retrograde from the emplaced tube and out of the mouth. Alternatively, the handle member may be a flat, curved blade, the distal end of which is removably coupled to the guide element and against which the orotracheal tube is temporarily held in preparation for intubation through the guide element.

In accordance with one aspect of the invention, blind orotracheal intubation may be safely and rapidly accomplished. To this end, the guide element preferably includes a posterior body portion including a bearing surface defining a portion of the channel wall along which an orotracheal tube may bear as it travels through the guide element and whereby the tube is directed properly towards the larynx. The bearing surface desirably includes an edge which fits against the upper edge of the posterior laryngeal cartilages and a projecting cusp aimed into the laryngeal opening to prevent overtravel of the tube into the rear edge of the larynx or beyond the back of the larynx and to center the guide element. Preferably, the recessed surface surrounding the lower end of the channel wall surrounds the bearing surface and cusp to enclose the rear and side edges of the laryngeal opening with the cusp extending into the interarytenoid incisure in the posterior edge of the laryngeal opening. In the embodiment wherein the upper portion of the guide element is an annulus, the body portion depends from the rear thereof. Further, certain of the anatomically contoured surfaces of the guide element preferably surround the laryngeal opening and embrace the larynx at a substantially gap-free junction such that the airway path extension is defined substantially exclusively between the larynx and either the upper surface of the annulus portion of the guide element or the lumen of the tubular handle member, depending upon which handle member is employed. As a consequence, an orotracheal tube inserted into the channel of the annulus portion will not readily pass into any other anatomical space at the back of the throat except the opening into the larynx, thus minimizing the possibility of misintubation.

The distal tip of an orotracheal tube is preferably releasably held within the handle lumen and/or guide element channel prior to insertion of the guide element into the patient's mouth. As the guide element is inserted, the remainder of the tube extends out of the mouth via the lumen of the tubular handle member or along the curved blade member. The guide element is easily, gently, and rapidly seated about the laryngeal opening, after which intubation is safely, rapidly and reliably accomplished merely by slidably advancing the tube further into the guide element whereupon it travels downward along the channel wall and is guided properly along the bearing surface toward and into the larynx and trachea. The guide element thus acts to guide the orotracheal tube into the larynx and trachea while obstructing access of the tube to the esophagus and other areas adjacent the larynx, thereby substantially reducing the risk of accidentally intubating these other areas.

In accordance with a further aspect of the invention, the body portion of the guide element preferably terminates at an occluding wall or tip below the bearing wall. The occluding wall is positioned relative the channel to overlie and substantially occlude the esophageal opening so as to block the passage of vomitus upward from the esophagus into the throat and larynx during intubation and to help prevent any tubular or elongated member inserted into the mouth after the guide element is seated from being accidently passed into the esophagus. Still further, the annulus portion of the guide element forward of the bearing wall preferably extends beyond the larynx to overlie anatomical features therearound so as to further minimize the risk of accidentally passing a tubular or elongated member, such as an orotracheal tube, into anatomical spaces surrounding the larynx.

In accordance with a yet further aspect of the present invention, esophageal intubation may also be readily accomplished with an esophageal tunnel through the body portion of the guide element. The body portion extends toward the esophagus such that the occluding wall or tip of the body portion preferably lies immediately above the esophageal opening. The tunnel passes through the body portion between the occluding wall and the upper surface of the upper or annulus portion of the guide element and is either accessible at the edge thereof, or continues into and through the tubular handle member and is accessible through an entrance hole along an upper edge of the handle member. The esophageal tunnel is positioned relative the channel wall such that when the channel wall is aligned with the laryngeal lumen, the esophageal tunnel is aligned and in close communication with the esophageal opening to define a substantially continuous path between the esophagus and the upper surface of the guide element. Preferably, the bearing surface creates a wall between the esophageal tunnel and the laryngeal wall extension or airway path to prevent communication therebetween whereby to minimize the possibility of erroneously inserting into the larynx a tube or other elongated member intended for the esophagus and vice versa. Moreover, provision of the laryngeal wall extension provides an airway path to permit continued patient breathing and/or a tube guideway for orotracheal intubation if necessary while or in conjunction with intubating or suctioning the esophagus so as not to accidently suffocate the patient.

An elongated or tubular member, such as a suction catheter, forceps or the distal viewing end of a fiberbundle of a flexible fiberoptic laryngoscope, is receivable through the esophageal tunnel for passage into or toward the esophagus. The distal end of such a member may be releasably held in the tunnel prior to insertion of the guide element into the patient's mouth. The guide element is easily and rapidly inserted into and seated in the throat while the remainder of the elongated or tubular member extends out of the mouth. After the guide element is seated at the back of the throat, the tubular-type member may then be advanced into the esophagus, if desired, by pushing it further into the esophageal tunnel such that the distal end passes beyond the tip of the guide element and into the esophagus.

In accordance with a further aspect of the present invention, a flexible or stylet-type fiberoptic laryngoscope may be rapidly and reliably aimed to allow visual examination of the larynx. In accordance with this aspect of the invention, a slant tunnel is provided in the guide element terminating in the laryngeal wall extension or airway path defined by the channel wall. The slant tunnel passes through the body portion and is either accessible through the top of the guide element or continues into and through the tubular handle member and is accessible through an entrance hole in the same manner as the esophageal tunnel. The distal end of a fiberbundle of the laryngoscope may be releasably secured in the slant tunnel of the guide element to provide a remote sight mechanism into the larynx upon seating of the guide element in the back of the throat. All the while, the channel wall maintains the laryngeal wall extension or airway path so as not to interfere with patient breathing. Additionally, an orotracheal tube may be advanced along the channel wall to accomplish orotracheal intubation which may be simultaneously viewed through the laryngoscope. Yet further, esophageal intubation may be accomplished with a separate esophageal tunnel passing through the body portion (and the handle member) as previously described without communicating with the fiberoptic laryngoscope slant tunnel.

In conjunction with the tubular handle member, a portion of the lumen at the proximal end of the handle member is exposed so that the user may quickly lay and hold the orotracheal tube in place therein and slidably advance the tube therealong into the channel of the guide element while at the same time manipulating the handle member to position the guide element. Additionally, the entrance hole to the esophageal and/or slant tunnels may be positioned at an exposed edge of the handle lumen to similarly hold a tubular-type member to be placed into the esophagus or for sighting into the larynx, respectively. The connector tip of an orotracheal tube is temporarily removed and the tube passed through the lumen of the handle member and into the guide element, and held in place at the exposed end of the handle lumen by the user's fingers as the guide element is emplaced. Additionally, or alternatively, a tubular-type member is inserted through the desired tunnel entrance hole and held in place at the exposed edge of the handle lumen. After seating of the guide element in the throat, the tube is released and advanced into the larynx or esophagus, as appropriate. Thereafter, the guide element may be withdrawn by retracting it over the emplaced tube, leaving behind the intubated tubular-type member. The connector tip may then be replaced on the exposed end of the orotracheal tube.

In conjunction with the blade handle member, the desired tubular or elongated member(s) may be held to the guide element by a clip or the like which holds the tubular-type member against the curved blade member with the distal end of the tubular-type member releasably held in the guide element. After seating of the guide element in the throat, the tubular-type member may be released from the blade clip and advanced through the guide element channel or tunnel into the larynx or esophagus as appropriate. Thereafter, the guide element may be withdrawn from the throat leaving behind the intubated tubular-type member. To allow for removal of the guide element over the tubular-type member, the guide element may be provided with a separable slit extending between the exterior surface of the guide element and the channel or tunnel, for example. Where the laryngoscope fiberbundle passes between the patient's teeth, it may be held against the curved blade handle member by a protective clip which protects the fibers from damage by the teeth. Where a tubular handle member is employed, the slant tunnel incorporated therein protects the fiberbundle as it passes between the patient's teeth.

The proximal end of the handle member may be provided with a support structure for supporting a laryngoscope body or handle to which the fiberbundle eyepiece end is connected. In this case, the laryngoscope body or handle may also serve as an alternative handle for the user, whereby to manipulate the conjoined laryngoscope and guide element.

By virtue of the foregoing, there is thus provided a guiding and aiming device to facilitate blind, gentle, rapid, accurate and selective guiding and aiming of tubular or elongated members relative a patient's larynx and esophagus, especially under emergency conditions. There is thus further provided a guiding and aiming device to facilitate blind, gentle, rapid, accurate, and selective intubation of the larynx and/or esophagus, substantially without risk of misintubation and without the drawbacks of the prior art. That is, using a guide element according to the principles of this invention, tubular or elongated members may be blindly and selectively aimed or introduced into the laryngeal or esophageal openings, in a rapid, gentle and reliable manner.

More specifically, intubation with the guiding and aiming device requires only a few seconds to accomplish; requires only a soft, semi-flexible guide element to be in contact with the patient's throat; is simple to use; is easy to learn and teach; is relatively inexpensive; does not require that the intubationist be positioned above the head of the patient, or that the patient's mouth be opened widely, or that the patient's neck be extended, or that assistants be present, or that substantial force be applied within the mouth or throat, or that larynx-obscuring fluids be suctioned out of the throat prior to intubation, or that a view of the larynx be secured; provides means to minimize the risk of misintubation; and is, thus, far more versatile and considerably safer than the currently accepted method of intubation with blade laryngoscopes.

These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 5 is a perspective view of the medical device of FIG. 1;

FIG. 7 is a diagrammatic illustration in partial longitudinal cross-section showing the matching of curved inner and outer contours of the curved, beveled edge of the larynx and adjacent structures with the medical device of FIG. 1;

FIG. 11 is a schematic illustration, partially cut-away, showing the modified medical device of FIG. 9 stabilized in the throat of a patient and supporting a battery-powered fiberoptic laryngoscope according to the principles of the present invention for laryngoscopic examination and intubation;

FIG. 12 is a schematic illustration showing the modified medical device of FIG. 9 supporting an externally lit fiberoptic laryngoscope;

FIG. 20 is a fragmentary, exploded, perspective view of the medical device of FIG. 19;

FIG. 20A is a top view of the guide element of the medical device of FIG. 19;

FIG. 21 is a schematic illustration, partially cut-away, showing the medical device of FIG. 20 stabilized in the throat of a patient;

FIG. 22 is a fragmentary, exploded, perspective view of a version of the guide element of FIG. 20 modified to receive the handle member anteriorly rather than posteriorly;

FIG. 24 is a perspective view of a version of the guide element of FIG. 20 modified to allow oroesophageal intubation and/or laryngoscopic examination.

FIG. 25 is a schematic illustration, partially cut away, showing the modified guide element of FIG. 24 stabilized in the throat of a patient according to the principles of the present invention for oroesophageal intubation;

FIG. 26 is a schematic illustration, partially cut away, showing the modified guide element of FIG. 24 stabilized in the throat of a patient and connected to a modified blade handle member supporting a battery-powered fiberoptic laryngoscope according to the principles of the present invention for laryngoscope aiming and stabilization;

FIG. 29 is a front perspective view of the bite protector clip of FIG. 26 along line 29—29 thereof.

DETAILED DESCRIPTION OF THE DRAWINGS

Figure 1:
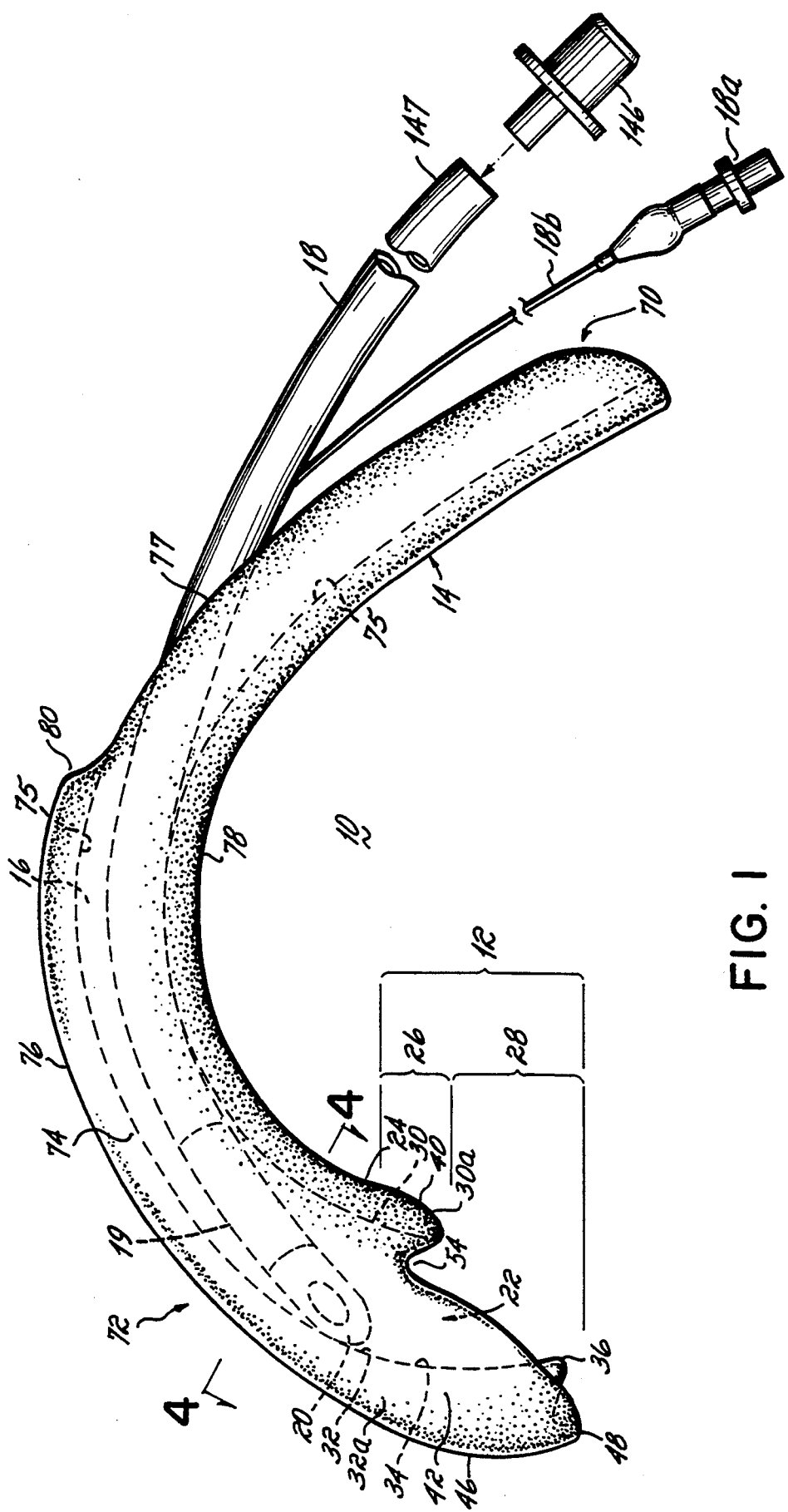
FIG. 1 is a side view of a first embodiment of a medical device according to the principles of the present invention with an orotracheal tube partially inserted therein and in preparation for orotracheal intubation.
Figure 2:
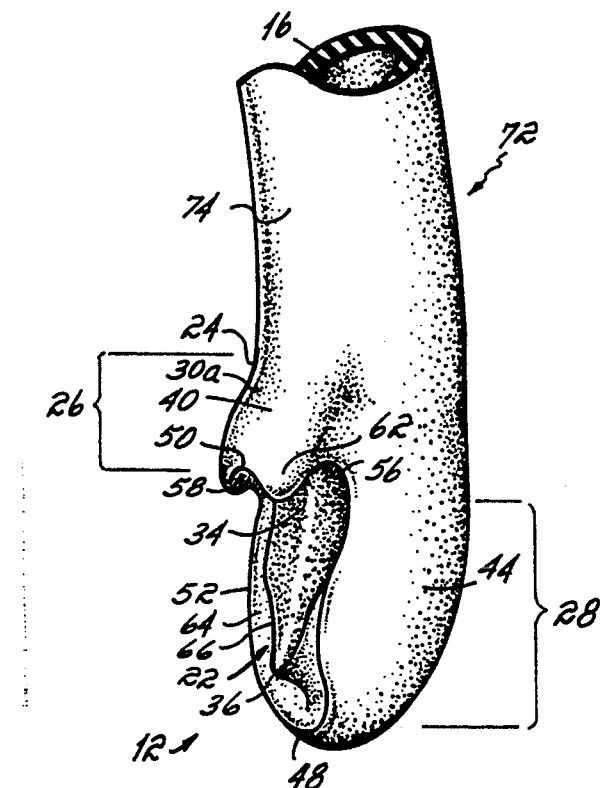
FIG. 2 is a right side, close-up, perspective view of the distal portion of the medical device of FIG. 1.
Figure 3:
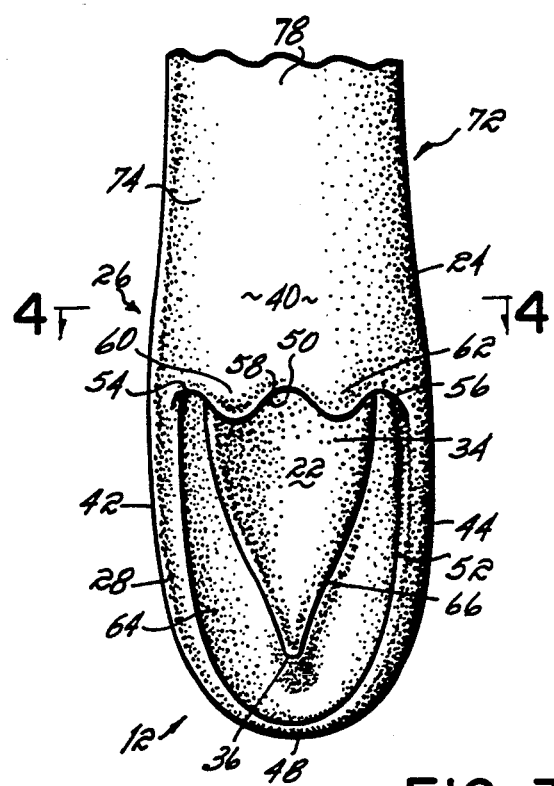
FIG. 3 is a front elevation view of the distal portion of the medical device of FIG. 1.

To assist the reader, included as an Appendix hereto is Table I setting forth the various items discussed herein and their related reference numerals, wherein like numerals in the various Figures refer to the same item.

With reference to FIG. 1, there is shown a first embodiment 10 of a medical device for blind orotracheal intubation according to the principles of the present invention. Medical device 10 includes a guide element 12 and a handle member 14 with a lumen 16 extending therethrough. Guide element 12 and handle member 14 may be integrally joined and are aligned such that an orotracheal tube 18 may be inserted, distal end 20 first, through lumen 16 and just past upper plane 24 between guide element 12 and handle member 14 and into channel 22 of guide element 12 coaxial with lumen 16. For use in adults, tube 18 may include an air injection port 18a in fluid communication with inflatable cuff 19 via pilot tube 18b as is conventional.

Guide element 12 preferably includes an upper annulus portion 26 through which channel 22 is defined, and a lower body portion 28 depending from the rear of annulus portion 26 posteriorly of channel 22. Channel 22 is defined through annulus portion 26 between an anterior wall 30 and posterior wall 32 both being gently curved in complementary fashion to define anterior and posterior arc portions 30a and 32a to annulus portion 26.

Figure 4:
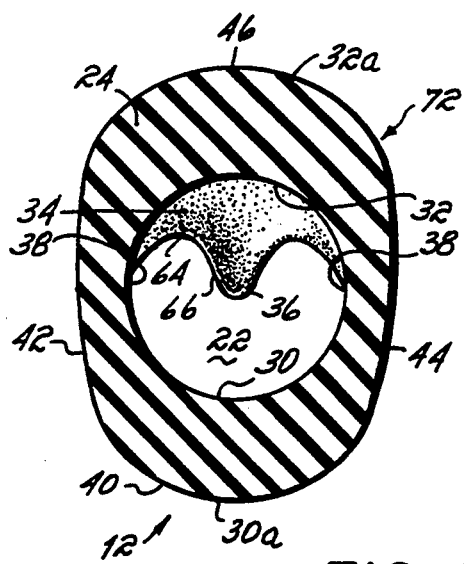
FIG. 4 is a cross-sectional view taken along line 4—4 of FIG. 1.

With further reference to FIGS. 2-5, it may be seen that posterior wall 32 of channel 22 extends beyond annulus portion 26 along a curved bearing surface 34 of body 28. Surface 34 preferably terminates in a projecting cusp 36. Posterior and anterior walls 32 and 30 preferably are continuous with channel sidewalls 38 therebetween (FIG. 4).

Depending from upper plane 24 of element 12 are generally smoothly continuous, exterior walls including front wall 40 anteriorly of channel 22, left and right outer walls 42, 44 outboard of channel 22 and curved rear wall 46 posteriorly of channel 22 and surface 34. Walls 40, 42, 44 and 46 cooperate to define exterior contour surfaces to guide element 12. More specifically, side and rear walls 42, 44, 46 merge at the bottom of element 12 to define a generally rounded occluding wall or tip 48 to body portion 28. Front wall 40 terminates in bottom undulating edge 50 which cooperates with continuous edge 52 of sidewalls 42, 44 to define left and right notches 54, 56. Undulating edge 50 of front wall 40 further defines a central notch 58 between a pair of mammillate nodules 60, 62. Guide element 12 further includes interior contour surfaces defined by the anterior wall 30 of channel 22 which merges smoothly into undulating edge 50 and by surface 34, cusp 36 and recessed surface 64 between sidewall edge 52 and edge 66 of surface 34.

Tubular handle member 14 includes a proximal end 70 and a forward end 72 which is joined to element 12 such that lumen 16 is continuous with channel 22. To this end, walls 40, 42, 44 and 46 of element 12 merge into and are continuous with outer wall 74 of handle member 14. Similarly, the walls 30, 32 and 38 of channel 22 merge into and are continuous with inner wall 75 of handle member 14 which defines lumen 16. The upper arcuate section 76 of wall 74 is cut away along segment 77 of the proximal end 70 of handle member 14 so as to expose part of lumen 16 along lower arcuate section 78 of wall 74 and to provide an exposed end or edge 80 to lumen 16. Orotracheal tube 18 may be held to medical device 10 by the operator (not shown) grasping handle member 14 about proximal end 70 so as to hold tube 18 in place against lumen wall 75 of lower arcuate section 78. Medical device 10 is preferably an integral one-piece unit of soft, semi-flexible, high strength silicon rubber, such as Silastic HS RTV available from Dow Corning, or other similar material which will not damage the soft tissue of the mouth or throat when manipulated thereagainst, as will be described, although handle member 14 may include stiffeners or other more rigid material so as to maintain its shape.

Figure 6:
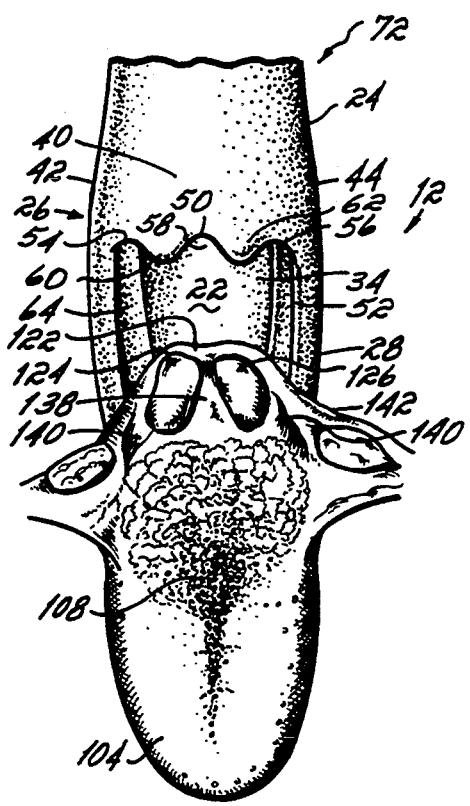
FIG. 6 is a fragmentary, partially schematic view of the medical device of FIG. 1 with the guide element about to be mated with anatomical features, shown in plan-front elevation, at the base of the tongue.
Figure 8:
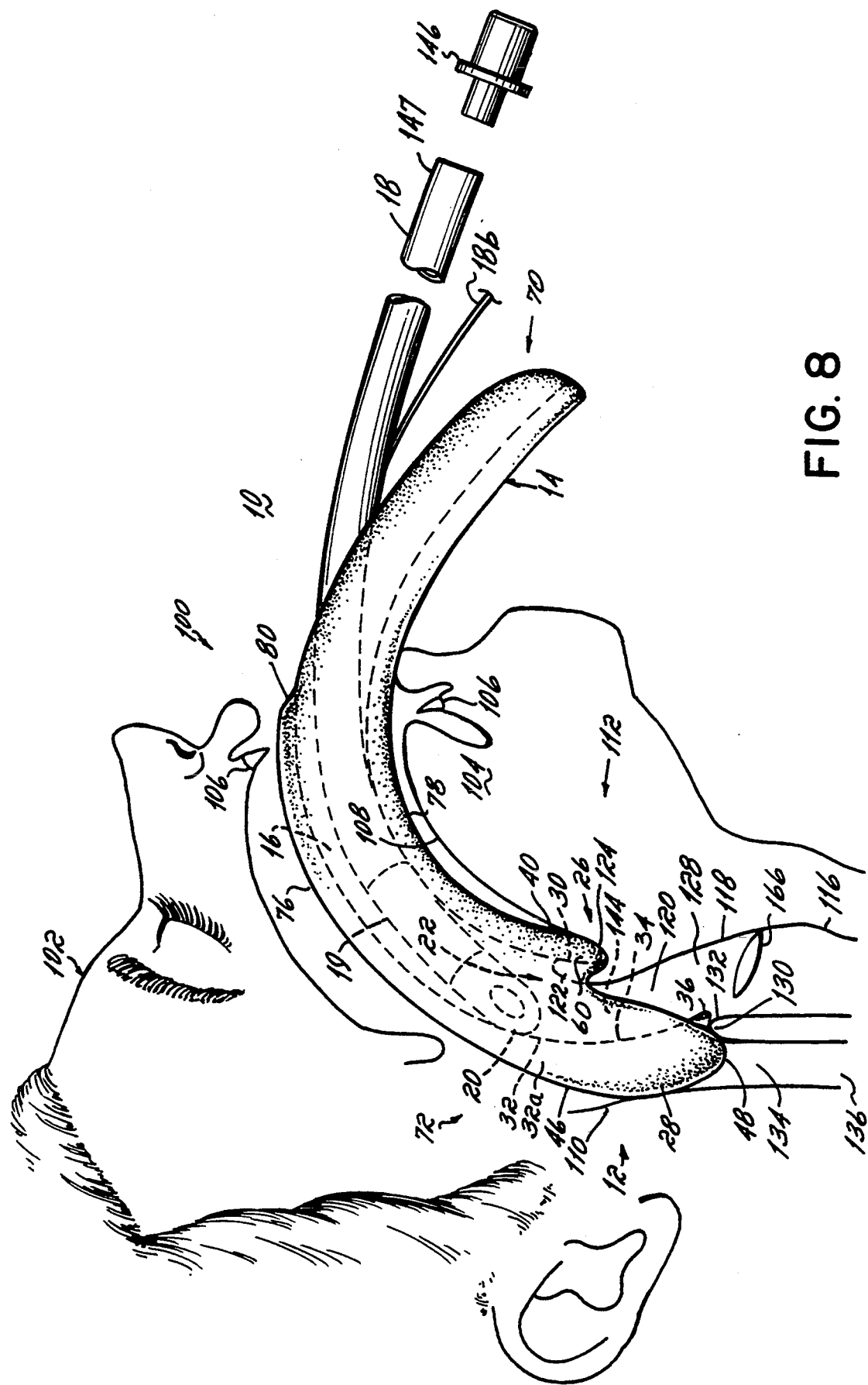
FIG. 8 is a schematic illustration, partially cut-away, showing the medical device of FIG. 1 stabilized in the throat of a patient.

In use, connector tip 146 is removed from the proximal end 147 of tube 18. Tube 18 is then laid into exposed portion 77 of lumen 16 and advanced along lumen wall 75 into guide element 12 such that distal end 20 of tube 18 is at least partially within channel 22 but, preferably, not extending below undulating front wall edge 50. Tube 18 is then held in place against lumen wall 75 by thumb or finger pressure of the user (not shown) as the user grasps the proximal end 70 of handle member 14. Proximal end 70 is then manipulated to place guide element 12 into mouth 100 of a patient 102 with guide element 12 rotated such that sidewall 42 or 44 is generally parallel tongue 104 (FIGS. 6–8). Handle member 14 is advanced to cause guide element 12 to pass between teeth 106 (FIG. 8) and over or beside tongue 104. Guide element 12 is advanced in the sideways position until it is past the hump 108 of tongue 104 after which element 12 is turned upright by manipulation of handle member 14 exteriorly of mouth 100. Handle member 14 is further manipulated to advance guide element 12 along the midline of the mouth toward posterior pharyngeal wall 110 at the back of throat 112 with front wall 40 sliding against tongue 104 and with channel 22 at about a 45° angle to the axis 114 (FIG. 7) of trachea 116 within larynx 118. Advancement of element 12 into throat 112 will be impeded or stopped by cooperation of one or more of the contour surfaces of element 12 and anatomical features at the back of throat 112 exteriorly of opening 120 into larynx 118. More specifically, element 12 will glide to a stop when:

(a) epiglottis 122 becomes hooked in channel 22 and contacts anterior wall 30 thereof;
(b) mammillate nodules 60, 62 slide into vallecular depressions 124, 126 at the back of tongue 104 and epiglottis 122 and are stopped thereby; and/or
(c) occluding wall or tip 48 butts up against posterior pharyngeal wall 110.

Once this impedance is sensed by the operator, the forward pressure on handle member 14 is stopped and, while exerting a gentle downward pressure on handle member 14 by manipulation of proximal end 70 so as to hold mammillate nodules 60, 62 in valleculae 124, 126, which serve as pivots, the lower tip 48 of body portion 28 is rotated anteriorly as far as it will go. Rear wall 46 of element 12 will glide slightly downward against posterior pharyngeal wall 110, and channel 22 and surface 34 will become aligned and contiguous with the tubular wall of larynx 118 so as to surround laryngeal lumen 128 where lumen 128 extends above posteriorly beveled edge 130 and behind epiglottis 122 of larynx 118. As seen in FIG. 8, tubular handle member 14 is curved to conform generally to the curvature between mouth 100 and larynx 118 to facilitate such manipulation. The foregoing rotation tends to bring firmly together all the contoured parts of guide element 12 and the matching anatomical features in throat 112. For example, the edge 66 of surface 34 is brought firmly against posteriorly beveled edge 130 of larynx 118 about laryngeal opening 120; the cusp 36 is brought firmly into interarytenoid incisure 132; epiglottis 122 lies tightly against anterior wall 30 of channel 22; lower tip 48 of body portion 28 of guide element 12 is brought directly over the opening 134 of esophagus 136; recessed surface 64 is brought firmly against the outer surface of edge 130 of larynx 118; central notch 58 is brought firmly astride the median glosso-epiglottic fold 138 (FIG. 6); and lateral notches 54, 56 are brought firmly astride lateral glosso-epiglottic folds 140 and pharyngo-epiglottic folds 142. Thus, it may be seen that (i) anterior and posterior arc portions 30a, 32a of annulus portion 26 surround the upper axial portion of laryngeal opening 120, and (ii) surface 34 of body portion 28 encloses the lower axial portion of laryngeal opening 120, and tip 48 of body portion 28 substantially occludes esophageal opening 134.

Even though perfect matching of the anatomically contoured surfaces of guide element 12 to anatomical features in throat 112 is not possible, the anatomical mating, i.e., the substantial approximation and interdigitation of these contoured parts with the corresponding anatomical contours, creates a sufficiently smooth tubular structure, with sufficient centering in the hypopharynx and sufficient alignment over the laryngeal opening 120 and sufficient occlusion of adjacent areas of the hypopharynx, to assure accurate, reliable guidance of orotracheal tube 18 exclusively into larynx 118 and trachea 116. Thus, when guide element 12 is properly seated around larynx 118 recessed surface 64, edge 66 and/or cusp 36 provide a supporting edge which is contiguous with at least the posterior edge of the laryngeal opening 120 as seen in Figures, such that, channel 22 and surface 34 are aligned and continuous with and effectively form an upward continuation of edge 130, epiglottis 122, and lumen 128 of larynx 118 to define a substantially exclusive airway path extension 144 (FIG. 8) around, atop and coaxial with laryngeal 128 with surface 34 defining an extension of the laryngeal wall upward from edge 130. The airway path also functions as a tube guideway thereby aligning distal end 20 of orotracheal tube 18 directly with lumen 128 of larynx 118. Meanwhile, opening 134 into esophagus 136 is occluded by tip 48 of body 28.

The size, annulus portion 26, and generally right-angled shape of guide element 12 help assure that annulus portion 26 will hook onto epiglottis 122 and settle into a secure position around larynx 118, rather than getting lost elsewhere in the hypopharynx or sliding down into esophagus 136. The anatomic contours of the guide element facilitate proper seating of the guide element around the larynx, and a relatively snug circumferential fit around, against and atop the tubular wall of the laryngeal opening, so that there will be no significant gaps between the guide element and larynx through which the tip of the orotracheal tube can migrate on its way through the guide element into the larynx and trachea. Orotracheal tube 18 can thereafter be advanced only into larynx 118 and trachea 116. Pre-lubrication of guide element 12 over its entire surface with a film of sterile, water-soluble medical lubricant, such as Surgilube available from Altana, Inc. in Melville, N.Y., minimizes any friction during insertion, mating of contours and passage of orotracheal tube 18.

When the operator senses, by gently but unsuccessfully attempting to move guide element 12 around in a plane perpendicular to the axis 114 of the larynx 118, that guide element 12 is firmly seated around larynx 118, finger pressure securing tube 18 against lumen wall 75 may be released and tube 18 advanced through lumen 16 and channel 22 into larynx 118 and trachea 116. Bearing surface 34 of wall 32 and body portion 28 cooperate with annulus portion 26 to confine the travel of orotracheal tube 18 to a smooth, curved pathway leading from mouth 100 directly towards larynx 118 and into laryngeal opening 120 aimed by cusp 36. The remainder of body portion 28 of guide element 12 tends to occupy the hypopharynx and wrap around larynx 118 in such a way as to further isolate the laryngeal lumen 128 and make adjacent areas impassable to an errant orotracheal tube 18.

Once tube 18 has been inserted far enough into trachea 116 so that cuff 19 has passed below vocal cords 166, air (usually 5-10 cc) such as from a standard medical syringe (not shown) is injected into air injection port 18a to inflate cuff 19 until it is in firm and circumferential contact with trachea 116 below vocal cords 166, thereby frictionally anchoring tube 18 in trachea 116. Guide element 12 is then withdrawn from throat 112 and mouth 100 by sliding element 12 retrograde over tubes 18 and 18b, and port 18a, while leaving orotracheal tube 18 frictionally secured in place in trachea 116 by inflated cuff 19. Connector tip 146 is then reinserted into proximal end 147 of tube 18 and connected to a respirator (not shown) whereby to ventilate the patient's lungs (not shown). The entire process of intubation, from the moment guide element 12 is inserted into mouth 100 until the moment when tube 18 is in place in trachea 116 and ready for attachment to a respirator, requires only a few seconds. Disposable medical device 10 may then be discarded.

Figure 9:
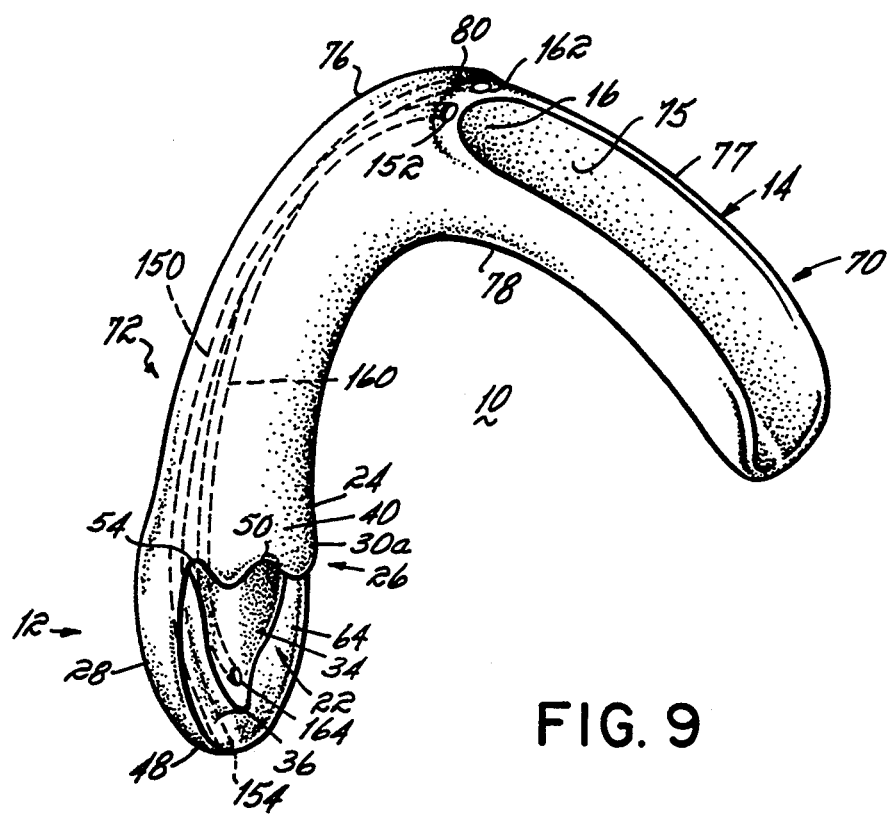
FIG. 9 is a version of the medical device of FIG. 1 modified to allow oroesophageal intubation and/or laryngoscopic examination.

As seen in FIG. 9, medical device 10 may be modified to include an esophageal tunnel 150 for esophageal intubation and/or a slant tunnel 160 for laryngoscopic examination as will be described. For purposes of explanation, medical device 10 will be described as modified to include both tunnel 150 and tunnel 160, although neither, one or both may be present.

Figure 10:
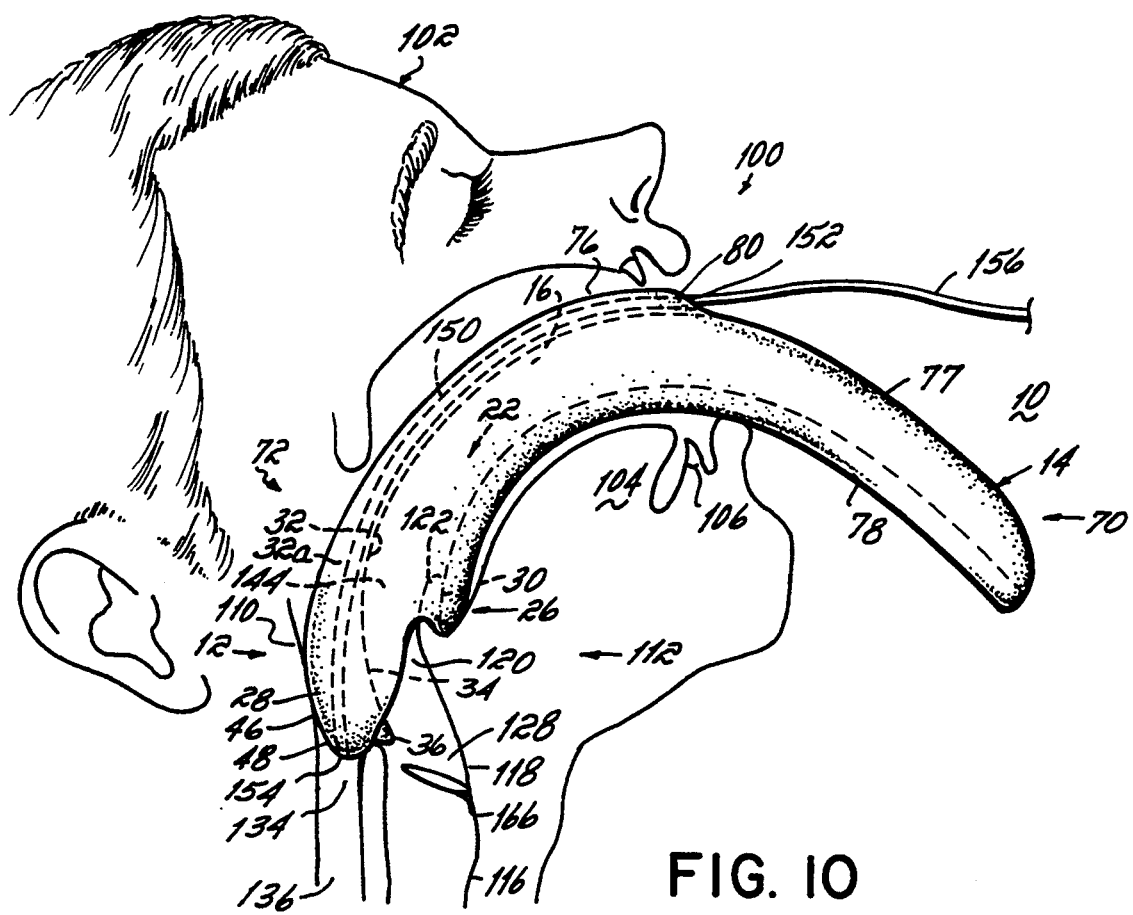
FIG. 10 is a schematic illustration, partially cut-away, showing the modified medical device of FIG. 9 stabilized in the throat of a patient according to the principles of the present invention for oroesophageal intubation.

With respect to oroesophageal intubation, and as seen in FIGS. 9 and 10, esophageal tunnel 150 extends through body portion 28 of element 12 and upper arcuate section 76 of handle member 14 between tip 48 and exposed edge 80. Tunnel 150 is accessible through entrance hole 152 (FIG. 9) on edge 80 and opens out of tip 48 at port 154 aligned with esophageal opening 134 when element 12 is stabilized in the throat 112 as seen in FIG. 10. Tunnel 150 is positioned posteriorly of surface 34 so as not to communicate with channel 22, thus avoiding the creation of a possible misintubation pathway within the guide element. A suction catheter or other similar tubular or elongated member 156 may be received through tunnel 150 for subsequent entry or aiming into esophageal opening 134. Once the guide element is stabilized in the back of the throat, tunnel 150 defines a path between edge 80 and esophageal opening 134 such that an elongated member 156 may be inserted into esophagus 136 for intubation thereof. During esophageal intubation, airway path 144 provided by channel 22 maintains breathability of the patient. Airway path extension 144 may also provide a tubular guideway as previously described.

With respect to laryngoscopic examination, and as seen in FIGS. 9 and 11, slant tunnel 160 extends through body portion 28 of element 12 and upper arcuate section 76 of handle member 14 between the posterior wall extension of channel 22 defined by bearing surface 34 and exposed edge 80. Tunnel 160 is accessible through entrance hole 162 on edge 80 and opens out of bearing surface 34 at port 164. Slant tunnel 160 is angled through body portion 28 obliquely downward relative channel 22 such that when guide element 12 is stabilized or seated at the back of the patient's throat, tunnel 160 aims obliquely into laryngeal opening 120 from its posterior aspect and at vocal cords 166 within larynx 118. Tunnel 160 also has a diameter slightly larger than the diameter of a fiberbundle 200 of a conventional battery-powered flexible fiberoptic laryngoscope 222 (FIG. 11) or an externally lit fiberoptic laryngoscope 224 (FIG. 12) so as to permit rapid slidable emplacement of distal end 226 of fiberbundle 200 therein. Fiberbundle 200 is removable from tunnel 160 by gentle traction.

Figure 13:
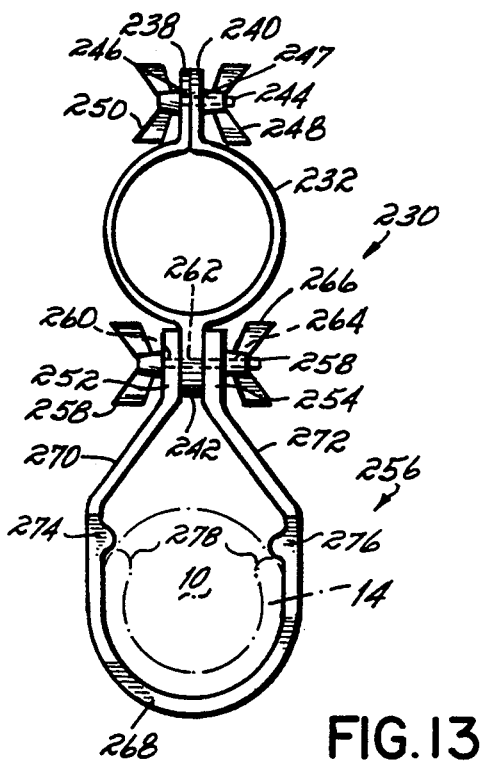
FIG. 13 is a front elevational view of the laryngoscope support of FIGS. 11 and 12.

A laryngoscope support 230 is provided over proximal end 70 of handle member 14 to hold laryngoscope 222 or 224 as will now be described with reference to FIG. 13. Support 230 includes a semi-flexible circular band 232 configured to surround and hold the handle 234 or control body 236 of fiberoptic laryngoscope 222 or 224, respectively. Band 232 opens in front into a pair of circular, parallel bolt brackets 238, 240 and has a single bolt bracket 242 projecting from the rear. Each of the bolt brackets has a hole through the center thereof for receiving a bolt therethrough. Brackets 238 and 240 are brought together by passing threaded bolt 244 through respective central holes 246 and 247 and rotating wing nut 248 onto bolt 244 which has a wing nut head 250. Rear bolt bracket 242 is interposed between two parallel bolt brackets 252,254, attached to the ends of cradle 256. Brackets 242, 252 and 254 are held in alignment together by wing nut headed, threaded bolt 258 passed through central holes 260, 262 and 264 of brackets 252, 242, and 254, respectively, and secured by rotation of wing nut 266 onto bolt 258.

Cradle 256 is comprised of a single, semi-flexible, U-shaped member 268 configured to slide around and onto proximal end 70 of handle member 14, and further includes two obliquely angled flat extensions 270, 272 extending between bolt brackets 252, 254 and top edges 274, 276 at opposite ends of U-shaped member 268. Top edges 274, 276 are inwardly curved to fit snugly over and against the edges 278 of exposed lower arcuate section 78 of handle member 14 when brackets 242, 252 and 254 are held together by bolt 258 and nut 266.

Support 230 may be adjusted as shown in FIG. 11 for laryngoscope 222 or as shown in FIG. 12 for laryngoscope 224. As is well understood, and as seen in FIG. 11, fiberbundle 200 extends between its distal tip 226 and its body-joining end 280, the latter being connected to body 282 of battery-operated, flexible fiberoptic laryngoscope 222. Scope 222 further includes a battery-containing handle 234 and a viewing eyepiece 286, as is conventional. Similarly, as shown in FIG. 12, laryngoscope 224 includes a control body 236 directly coupled to end 280 of fiberbundle 200. Control body 236 also supports an eyepiece 290 and connects to an external light source (not shown) via fiberbundle 292.

To use medical device 10 for laryngoscopy, the laryngoscope is secured to handle member 14 by inserting proximal end 70 of handle member 14 into cradle 256. The angle of support 230 is adjusted to accommodate the type of flexible fiberoptic laryngoscope to be used. This is accomplished by loosening wing nut 266 on bolt 258, rotating band 232 to the desired vertical angle with respect to cradle 256, and then retightening wing nut 266 which also tightens cradle 256 to handle member 14. Next, flexible fiberbundle 200 is passed, distal tip 226 first, through entrance hole 162 on edge 80 until distal tip 226 of the fiberbundle is flush with or just behind posterior wall extension 34 of channel 22 at port 164. Thereafter, guide element 12 may be inserted into the throat as previously described and laryngoscopy undertaken. Additionally, oroesophageal and/or laryngeal intubation may be undertaken as previously described. Thus, if intubation is to be performed, an orotracheal tube 18 may be included.

When guide element 12 is seated in its proper position around larynx 118, distal tip 226 of fiberbundle 200 will be pointed directly at vocal cords 166, and will be stabilized in that position by tunnel 160 which owes its own stability to the matching contours of guide element 12 and anatomical features in throat 112, which enable guide element 12 to attain a secure seat around and against the larynx. The light source of the laryngoscope is then turned on and, looking through eyepiece 286 or 290, fine aiming adjustments can then be made by gently manipulating medical device 10 under direct vision. If an orotracheal tube 18 is within lumen 16, tube 18 may now be advanced downward through guide element 12 while the distal end 20 of tube 18 is monitored through the laryngoscope eyepiece. As end 20 approaches and passes between the vocal cords 166, a stable image thereof is being transmitted along fiberbundle 200 to the eyepiece. Thus, visualization of the process of orotracheal intubation, as well as visually-assisted manipulation of other tubular devices within the larynx, are possible with medical device 10 positioned as described. It can be readily seen that slight variations in the location and angle of slant tunnel 160 within guide element 12 would allow visual and operative access to other areas both within and adjacent the larynx.

Figure 14:
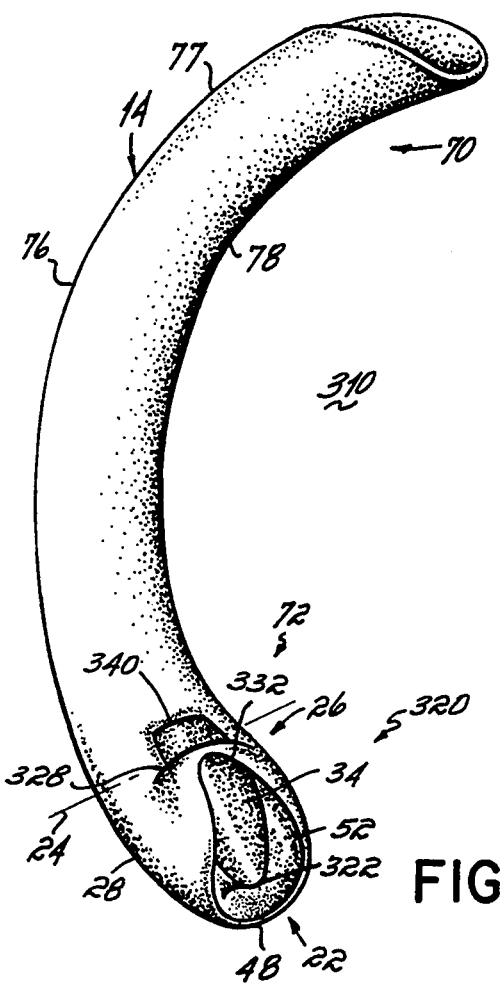
FIG. 14 is a perspective view of a second embodiment of a medical device in accordance with the principles of the present invention suitable for orotracheal intubation of an infant.
Figure 15:
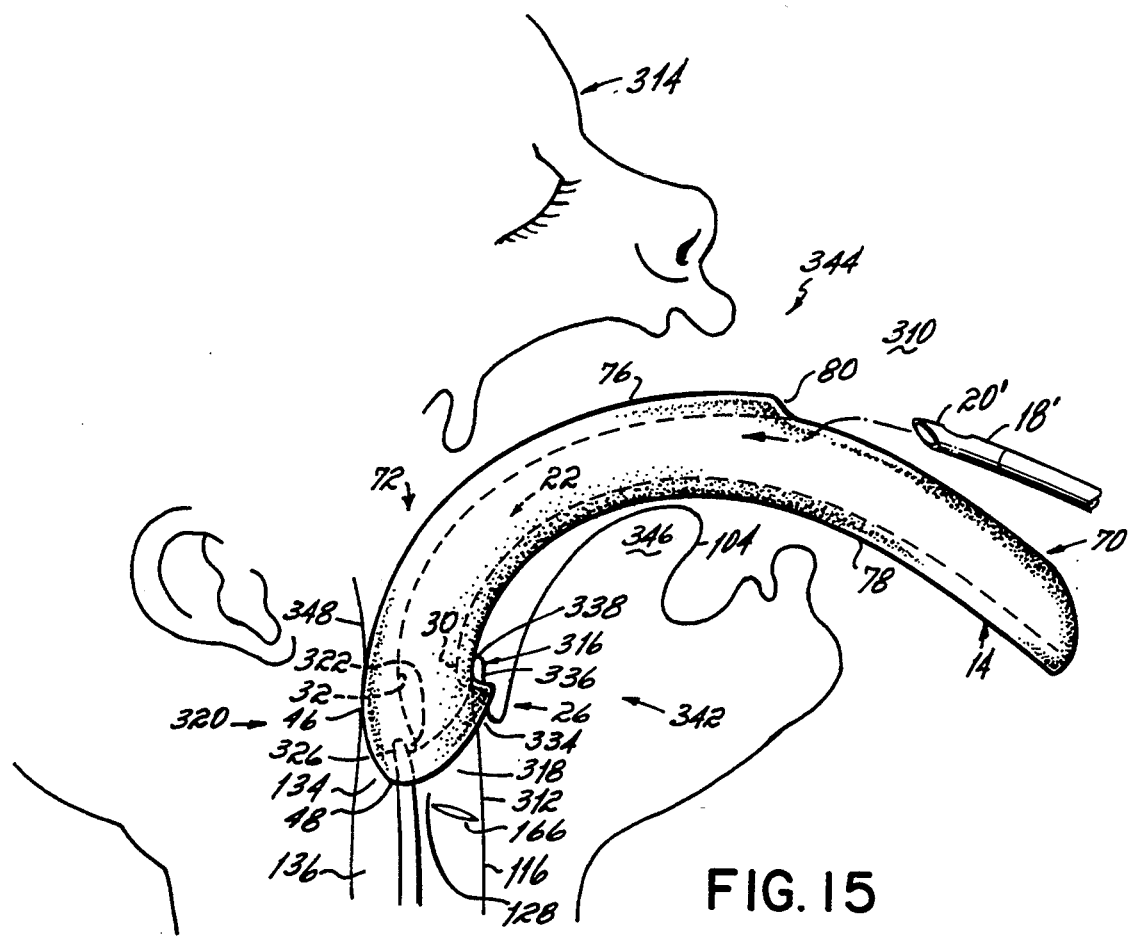
FIG. 15 is a schematic illustration, partially cut-away, showing the medical device of FIG. 14 stabilized in the throat of an infant.

With reference to FIGS. 14 and 15, there is shown a second embodiment 310 of a medical device particularly suited to intubating the larynx and trachea of infants in accordance with the principles of the present invention. Medical device 310 is similar in structure and operation to medical device 10, and may be similarly modified for oroesophageal intubation and/or laryngoscopic examination. However, medical device 310 is somewhat structurally different from medical device 10, as noted below, to take into account the smaller, softer and less defined larynx 312 of an infant 314 when compared to an adult (such as patient 102 in FIG. 8). Not only is there less useful anatomical detail, the epiglottis 316 is quite floppy and can, thus, be pushed backwards over the laryngeal opening 318 thereby preventing intubation. To these ends, guide element 320 of device 310 is smaller than guide element 12 of device 10. Further, posterior wall 32 of channel 22 of guide element 320 includes an elliptical lower edge 322, but does not include a cusp. Instead, channel 22 is angled so that elliptical lower edge 322 will fit over the posterior laryngeal cartilages 326 and preferably slightly inside laryngeal opening 318 much like a shoehorn, as seen in FIG. 15. Also, front wall 328 of annulus portion 26 of guide element 320 is generally short and thin, and has an inverted U- or V-shaped interior edge 332 so as to slide around the general U- or V-shaped floppy epiglottis 316 of an infant 314. Inferior edge 332 will thus engage only the base 334 of anterior surface 336 of epiglottis 316 while avoiding any pressure on its floppy tip 338. Note that unlike medical device 10, guide element 320 of medical device 310 preferably does not include mammillate nodules or lateral notches. Note also that annulus portion 26 of element 320 is not completely continuous with handle member 14, but instead is separated anteriorly by a generally rectangular cutout 340 adjacent front wall 328 just above upper plane 24 through which tip 338 of epiglottis 316 may project and be protected. Tip 338 might actually protrude into cutout 34 just barely above upper plane 24. However, epiglottis 316 is exaggerated in FIG. 15 with tip 338 shown extending well beyond plane 24 merely for purposes of explanation.

In use, medical device 310 is loaded with an infant orotracheal tube 18' from which the connector tip (not shown) has been removed (similar to that shown in FIG. 1 with respect to tube 18) and placed into the infant's throat 342 through its mouth 344 as in the use of medical device 10, but with front wall 328 sliding against tongue 346 until inferior edge 332 is stopped around and against base 334 of epiglottis 316; wall 46 of guide element 320 abuts and is stopped by posterior pharyngeal wall 348; and/or lower edges 322 and tip 48 are stopped by posterior cartilages 326 of larynx 312. Slight elevation and forward pressure on proximal end 70 of handle member 14 will then bring rear wall 46 securely against posterior pharyngeal wall 348 and properly orient channel 22 relative laryngeal opening 318. Slight downward pressure exerted on guide element 320 will insure that it is seated securely around and against cartilages 326 surrounding laryngeal opening 318. Intubation may then proceed as described in connection with tube 18 and medical device 10.

Figure 16:
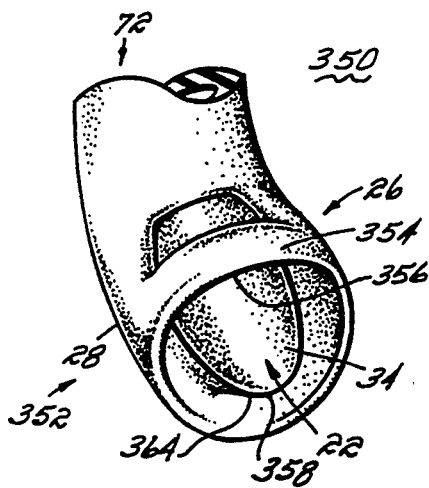
FIG. 16 is a perspective view of a third embodiment of a medical device according to the principles of the present invention.
Figure 17:
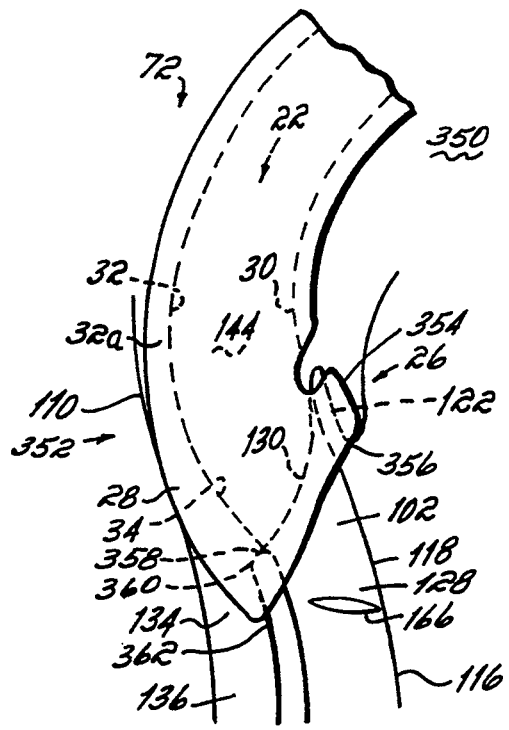
FIG. 17 is a schematic illustration, partially cut-away, showing the medical device of FIG. 16 stabilized in the throat of a patient.

With reference to FIGS. 16 and 17, there is shown a third embodiment 350 of a medical device similar to medical device 310, but made larger and modified slightly for an adult larynx 118. Guide element 352 thereof is larger than guide element 320 and front wall 354 is broader and taller than front wall 328 (FIG. 14), and includes a generally flat, smooth inferior edge 356. Also, lower edge 358 of posterior wall 34 is curved to conform generally to the circumferential curvature of posterior edge 360 of laryngeal opening 120 so that when guide element 352 is inserted into throat 112, edge 358 will fit against or just above edge 360 of the posterior laryngeal cartilages 362. Similarly, lower anterior surface 364 below edge 358 of wall 34 is curved to fit snugly against posterior laryngeal cartilages 362. Operation and use of medical device 350 is substantially identical to that of medical devices 310 and 10, and may optimally include an oroesophageal tunnel and/or a slant tunnel (neither shown in FIGS. 16 and 17).

Figure 18:
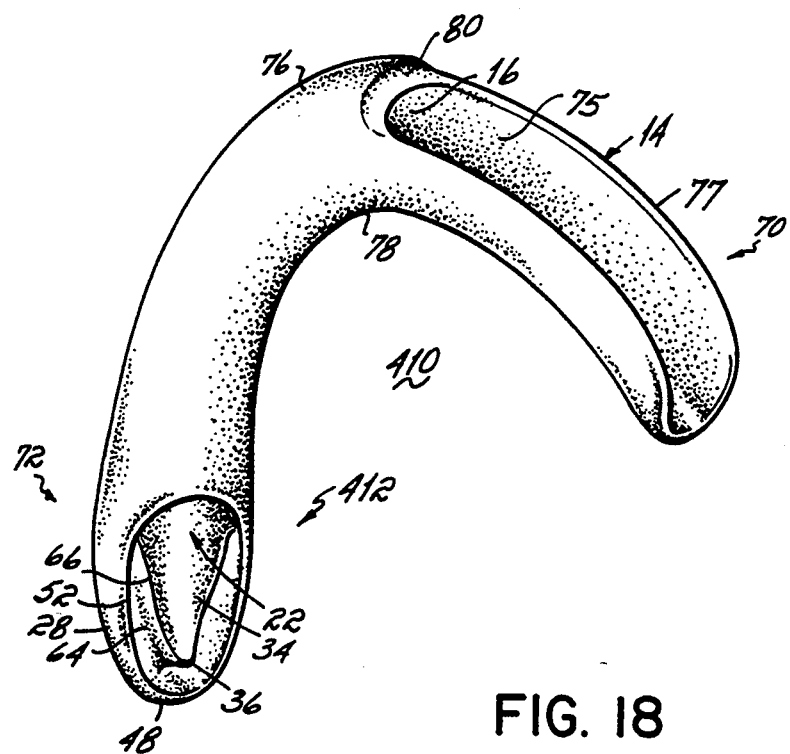
FIG. 18 is a perspective view of a fourth embodiment of a medical device in accordance with the principles of the present invention.

FIG. 18 shows a fourth embodiment 410 of a medical device in accordance with the principles of the present invention. Medical device 410 is substantially identical to medical device 10, except that guide element 412 lacks a front wall completing the annulus portion 26 and, thus, lacks structure to engage epiglottis 122 or to surround edge 130 of larynx 118. Use of device 410 is substantially like that of medical device 10, but is initially inserted until occluding wall 48 of body portion 28 butts up against posterior pharyngeal wall 110 whereafter handle member 14 is rotated upwardly to rotate guide element 412 into a more vertical position and downward pressure then applied to seat guide element 412 in the throat about larynx 118.

Although guide element 412 of medical device 410 does not have an annulus to surround the laryngeal opening to define the airway path, the curvature of surface 34, along with the curvature of lumen 16 in handle member 14, cooperates with the intrinsic curvature of tube 18 to sufficiently confine the travel of an orotracheal tube to an axis leading directly into the larynx and trachea thereby reducing the likelihood of misintubation.

Figure 19:
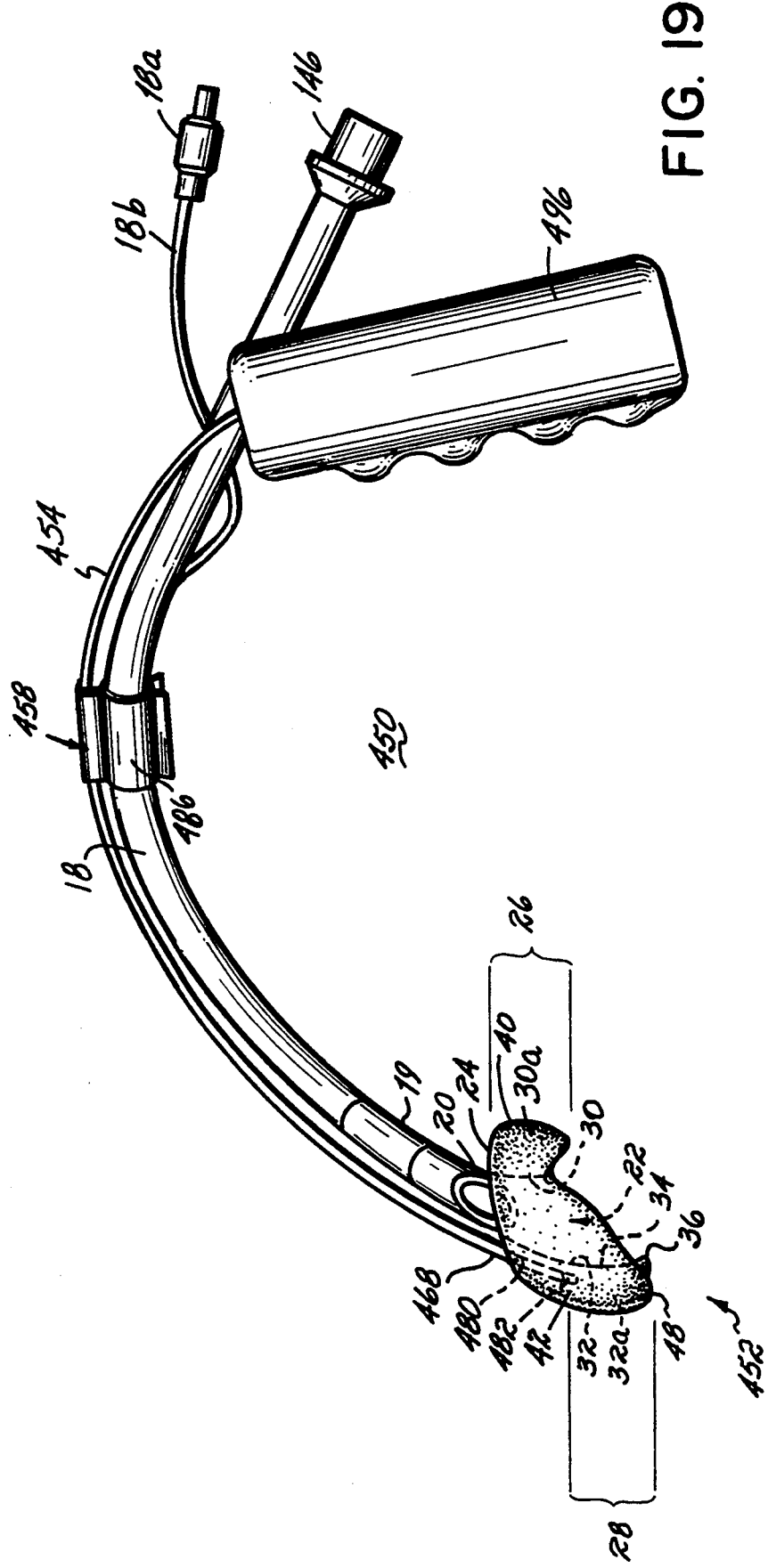
FIG. 19 is a side view of a fifth embodiment of a medical device according to the principles of the present invention.

With reference to FIGS. 19–21, there is shown a fifth embodiment 450 of a medical device in accordance with the principles of the present invention. Medical device 450 includes a guide element 452 which is substantially identical to guide element 12 except that upper plane 24 defines the top surface of the guide element. Similarly, edge 66 of surface 34 may have a more pronounced curvature adjacent cusp 36 as seen in FIGS. 19–21. A curved blade handle member 454 is curved to conform generally to the curvature between mouth 100 and larynx 118, and is releasably attached to guide element 452, as will be described hereinafter. An orotracheal tube 18 may be held against blade 454 by a blade-tube clip 458 with distal end 20 just entering channel 22 of guide element 452.

For access to channel 22 of guide element 452 through front wall 40 of annulus portion 26 thereof, a slit 460 (FIG. 20A) is preferably provided extending between channel anterior wall 30, guide element front wall 40, top surface 24, and central notch 58 whereby to define two openable panels 462, 464 of front wall 40 as seen in FIG. 22. Panels 462, 464 are preferably held together by a small portion 466 of front wall 40 to define a tack point. Alternatively, tack point 466 could be comprised of a biologically acceptable glue or similar tacky material placed at the borders of panels 462, 464.

Figure 23:
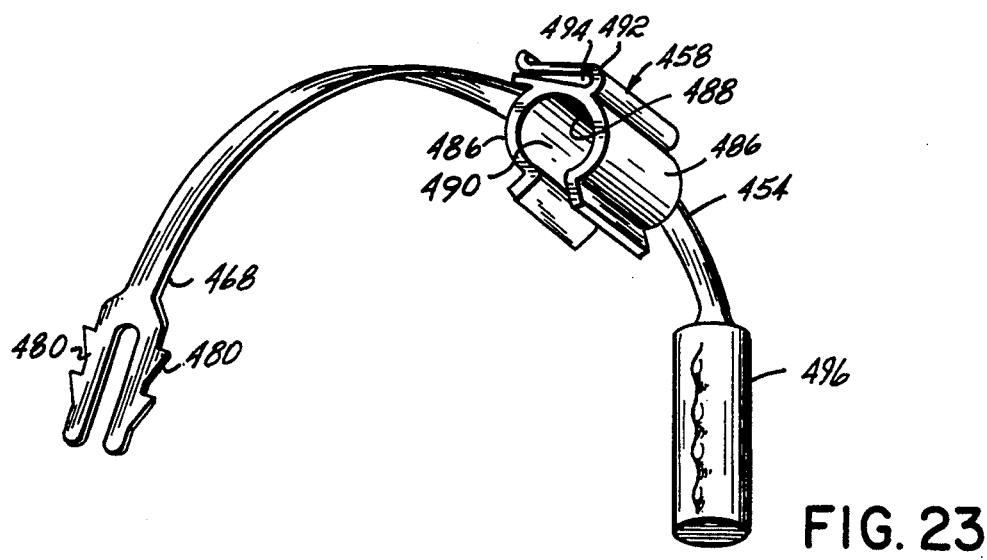
FIG. 23 is a perspective, exploded view of the blade handle member and blade-tube clip of FIG. 20.

The distal end 468 of blade handle member 454 is preferably held to guide element 452 at the rear of the annulus portion 26. To this end, distal end 468 is forked to define a pair of toothed prongs 480 as seen in FIGS. 20 and 23 which are receivable in sockets 482 (FIG. 20) defined through top surface 24 of guide element 452 and into body portion 28 thereof. The silicon rubber body of guide element 452 allows for an interference fit of prongs 480 within sockets 482 as represented by phantom lines 484 in FIG. 20.

With further reference to FIG. 23, it may be seen that blade-tube clip 458 is provided with a pair of arcuate spring walls 486 joined at base wall 488 to define a tube-holding space 490. Tube 18 is held by clip 458 by inserting the tube between spring walls 486 as is well understood. Clip 458 is held to blade 454 by a resilient flange 492 also joined to base wall 488 to define a generally flat receiving slot 494 into which a flat portion of blade handle member 454 between distal end 468 and a handle 496 attached to the proximal end thereof is grippingly received.

In use of medical device 450, blade-tube clip 458 is slid onto blade 454 and tube 18, with its distal end 20 entering channel 22, attached to clip 458. The combination of medical device 450 and tube 18 is then inserted into the mouth 100 and manipulated by handle 496 until seated as previously described in connection with medical device 10. When the operator senses that guide element 452 is firmly seated around larynx 118 (FIG. 21), orotracheal tube 18 may be released from clip 458 and advanced through channel 22 into larynx 118 and trachea 116 as previously described. Once tube 18 is inserted to the extent desired, it may be connected to a respirator (not shown) via connector tip 146 and the patient's lungs (not shown) ventilated thereby. Guide element 452 may then be withdrawn from throat 112 and mouth 100 by reversing the motion used to insert it therein. Alternatively, guide element 452 may be withdrawn prior to attaching tube 18 to a respirator.

After guide element 452 has been withdrawn from mouth 100, annulus portion 26 still surrounds a portion of tube 18. To release tube 18 from the embrace of annulus portion 26, the small tack point 466 is manually broken by pulling the two panels 462, 464 apart at slit 460 to release tube 18 therethrough. Guide element 452 may be removed from blade 454 by forcibly pulling prongs 480 from sockets 482. This pulling force causes the silicone rubber sockets 482 to deform sufficiently to release the barbs or teeth of prongs 480. Disposable guide element 452 may then be discarded. If the blade 454, clip 458, and handle 496 are made of a single piece of inexpensive plastic, they may also be discarded.

It will be appreciated that blade 454 could be releasably held to guide element 452 by inserting prongs 480 into sockets 482' formed in panels 462', 464' anteriorly of the guide element modified as 452' in FIG. 22 rather than posteriorly as shown in FIG. 20. Also, clamp 458 will be mounted to blade 454 upside down such that orotracheal tube 18 follows over the top of blade 454 and down into channel 22 rather than from below the blade member as seen in FIG. 20. To accommodate receiving prongs 480 of blade 454, the guide element is modified so that its front wall 498 is taller than front wall 40 and rear wall 499 is shorter than corresponding rear wall 46.

With reference to FIG. 24, it may be seen that guide element 452 may be modified to include an esophageal tunnel 150 for esophageal intubation and/or a slant tunnel 160 for laryngoscopic examination. Tunnel 150 extends through body portion 28 to provide a communication path between entrance hole 152 on top surface 24 and port 154 at the end of tip 48 of guide element 452, and is otherwise identical to esophageal tunnel 150 of medical device 10. Similarly, slant tunnel 160 extends between an entrance hole 162 adjacent rear wall 46 and top surface 24 and port 164 along bearing surface 34, and is otherwise identical to slant tunnel 160 previously described.

Figure 27:
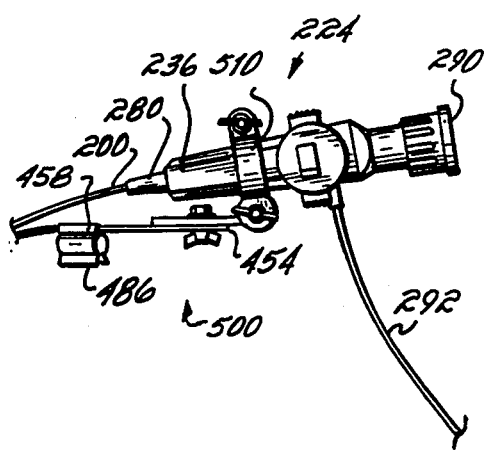
FIG. 27 is a schematic illustration showing the modified medical device of FIG. 26 supporting an externally lit fiberoptic laryngoscope.
Figure 28:
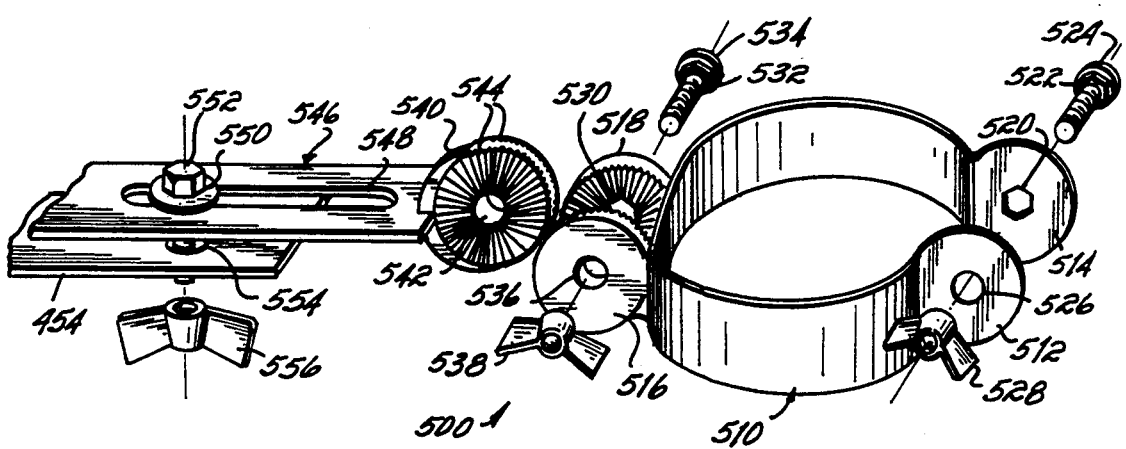
FIG. 28 is a fragmentary, exploded, perspective view of the laryngoscope support of FIGS. 26 and 27.

For laryngoscopy, blade 454 is modified as seen in FIGS. 26–28 primarily by replacing handle 496 with a laryngoscope support 500 (FIG. 28). Further, to prevent a patient from biting the delicate fibers contained in fiberbundle 200 as it passes between the patient's teeth 106, it is preferably first passed through a bite-protector clip 502. As seen in FIG. 29, clip 502 is an elongated member having a generally tubular port 504 extending longitudinally therethrough, through which is receivable fiberbundle 200. Clip 502 further includes a generally rectangular port 506 extending longitudinally therethrough and slidably receiving blade 454 therethrough. Preferably, clip 502 is provided a slot 508 along one edge to permit clip 502 to be slid laterally on or off blade 454. Clip 502 is preferably made of semi-rigid plastic to protect the fiberbundle, and is covered with a layer of soft pliable plastic material to cushion any contact with the patient's teeth 106.

With reference to FIG. 28, support 500 includes a semi-flexible circular band 510 configured to surround and hold handle 234 or control body 236 of fiberoptic laryngoscope 222 or 224, respectively. Band 510 opens in front into a pair of circular, parallel bolt brackets 512, 514, with another pair of circular, parallel bolt brackets 516, 518 attached to the rear. Each of the bolt brackets has a hole through the center thereof for receiving a bolt therethrough. Hole 520 of bracket 514 has a hexagonal shape to receive the non-turning head 522 of threaded bolt 524 therethrough, while hole 526 of bracket 512 is round, as is conventional. Brackets 512, 514 are brought together by rotation of wing nut 528 on threaded bolt 524, as is well understood. Similarly, bracket 518 has a hexagonal hole 530 to receive non-turning head 532 of threaded bolt 534 therethrough, the remainder of bolt 534 passing through round hole 536 of bracket 516 to be threadably received into wing nut 538.

Interposed between rear bolt brackets 516, 518 is tongue member 540. Tongue member 540 has a generally circular shape and fits between bolt brackets 516 and 518. Tongue member 540 has a round hole 542 in the center for accepting threaded bolt 534 therethrough. The inner circular faces of rear bolt brackets 516, 518 and both circular faces of tongue member 540 are radially serrated as at 544. Tongue member 540 is attached to horizontal fillet 546 having a longitudinal slot 548 in the center sized to accept in non-rotational relationship non-turning head 550 of threaded bolt 552 which passes downwardly through a hole 554 in the proximal end of blade 454. Bolt 552 threadably cooperates with wing nut 556 to secure support 500 to blade 454. Support 500 may be adjusted as shown in FIG. 26 for laryngoscope 222 or as shown in FIG. 27 for laryngoscope 224.

To use medical device 450 for laryngoscopy, a guide element 452, with slant tunnel 160 of a diameter slightly larger than that of the fiberbundle which will be inserted into it, is selected and pushed onto blade prongs 480 of blade 454. If intubation is going to be performed in addition to laryngoscopy, blade-tube clip 458 is pushed onto and across blade 454 from the edge. Bite protector blade clip 502 is also pushed onto blade 454 from the edge thereof at a point on the blade where the blade is likely to be situated between the patient's teeth 106 when guide element 452 is in the throat (see FIG. 26). The angle of support 500 is adjusted by loosening wing nut 538 on bolt 534, rotating band 510 to the desired vertical angle with respect to fillet 546, and the retightening of the wing nut. The laryngoscope is then secured to support 500 by inserting it into band 510 and tightening bolt 524. Fiberbundle 200 may then be fed through port 504 of clip 502 and into tunnel 160 through entrance hole 162. To take up any slack in the fiberbundle, the distance from guide element 452 to the laryngoscope may be adjusted by loosening wing nut 556 on bolt 552, sliding fillet 546 along, or turning it horizontally around, bolt 552 in slot 548, as the case may be, until the desired tightness of the fiberbundle and the desired horizontal angle of the laryngoscope with respect to blade 454 are achieved, and then retightening wing nut 556. Thereafter, guide element 452 may be inserted into the throat and laryngoscopy, and/or esophageal and/or tracheal intubation undertaken as previously described.

The guide element for all embodiments of the invention may be made of a soft, high-strength silicone rubber, which is preferably supplied pre-lubricated over its entire surface with a thin film of biocompatible, water-soluble lubricating gel, and may be contained in a sealed wrapper to protect the lubricating film and to assure cleanliness of the guide element. The blade, blade-tube clip, bite-protector clip, handle and/or tubular handle member can each be made separately of metal or plastic, or can be fabricated together as a single piece of inexpensive, disposable plastic. The laryngoscopic support can also be fabricated in either metal or plastic.

A form for a guide element suitable for a particular size of human or animal throat may be constructed by making a mold around a representative cadaveric larynx (or anatomical model thereof) of the desired size and species which has a relatively large, smooth curved tube inserted into it from the oral cavity. Preferably, the tube has as large an outer diameter as the laryngeal lumen will accommodate. The tube is inserted and extends in a gradual, smooth arc from the interior of the larynx upward and forward toward and at least into an area defining a mid-portion of the oral cavity. If the tubular handle member is desired, the tube also extends through the mouth to a point at least one hand-breadth (about 8 centimeters) outside the mouth so as to form the basis for a handle member of sufficient length for grasping and to define a lumen running therethrough. Thereafter, a mold is made around and above the larynx (and around the tube for the tubular handle member if desired) such that the resulting mold incorporates an impression of the anatomy of and surrounding the larynx (and of the tube, if desired). A trowelable, urethane compound such as Flexane 80 putty, available from Devcon Corporation in Danvers, Mass., may be used to construct the mold. When the mold hardens, it is removed. When the tube is withdrawn from the larynx and the hardened mold, it leaves in the mold a smooth, continuous, curved, tubular passageway leading directly into the larynx and trachea, along which any tube of smaller diameter (than the original tube) may be blindly guided into the trachea.

The anatomical details of the larynx and surrounding structures and spaces are permanently impressed into the distal surfaces of the mold, so that when the mold is removed from the throat and its distal end is refined into a suitable guide element, as described below, the guide element can be quickly oriented into position merely by easing it into the hypopharynx. Since the mold represents a three-dimensional negative image of the larynx and hypopharynx, it quickly settles/pops into perfect alignment thereagainst.

To facilitate rapid insertion of the guide element into the throat, sharp edges and corners can be rounded and reduced in size. Some features may even be eliminated, as long as enough mating detail is maintained to assure a properly oriented and snug fit against the larynx, so that a tube being inserted through the tubular passageway and into the larynx cannot deviate away from the orotracheal axis and wander into other areas of the hypopharynx. Where the tubular handle member 14 is integral with element 12, upper arcuate section 76 of proximal end 70 may be cut away to expose edge 80. After the mold (with or without an integral handle member) has been refined as described, guide elements and/or medical devices may be reproduced by conventional methods in any desired material.

Tunnels running from the upper portion of the mold or guide element downward toward either the larynx or the esophagus may be drilled or molded as desired.

By virtue of the foregoing, there is thus provided a guiding and aiming device to facilitate blind, gentle, rapid, accurate and selective guiding and aiming of tubular or elongated members relative a patient's larynx and esophagus, especially under emergency conditions. There is thus further provided a guiding and aiming device to facilitate rapid, gentle, and blind oral intubation of the larynx and/or esophagus, without substantial risk of misintubation and without the drawbacks of the prior art. That is, using a guide element according to the principles of this invention, tubular or elongated members may be blindly and selectively aimed or introduced into the laryngeal or esophageal openings, in a rapid, gentle, and accurate manner.

While the present invention has been illustrated by the description of various embodiments and while the embodiments have been described in considerable detail, it is not the intention of applicant to restrict or any way limit the scope of the appended claims to such detail. Additional advantages and modifications will readily appear to those skilled in the art. For example, the medical devices disclosed herein are shown in use in a human throat. The invention has applicability to other animals having a mouth and a larynx, for example. Moreover, the shapes, materials, and arrangements of the components of the various embodiments disclosed herein may be readily altered as necessary. For example, the surface contours of and tunnels within the guide element may be added to or reduced. The tunnel for aiming a laryngoscope fiberbundle into the larynx may have its terminus in the cusp, rather than the bearing surface. The guide element alone may be directly attached to the tip of a stylet-type fiberoptic laryngoscope, the handle or body of which may be used, in lieu of the tubular handle member, to insert and manipulate the guide element in the throat. The guide element may also be made in a skeletal rather than a solid form, or as a collapsible or inflatable device which is expanded or inflated before or after being inserted into the throat. The tack point, when used, may also be eliminated and the position of the slit shifted away from the mid-line of the guide element. Where a tubular handle is joined to the guide element, the slit may be extended through and along the length of a wall of the handle so that the handle may also be opened to release a tube contained therein. The invention in its broader aspects is, therefore, not limited to the specific details, representative apparatus and method, the illustrative examples shown and described. Accordingly, departures may be made from such details without departing from the spirit or scope of applicant's general inventive concept.

APPENDIX

TABLE I

| Reference Number | Item |
| --- | --- |
| 10 | first embodiment of a medical device |
| 12 | guide element |
| 14 | tubular handle member |
| 16 | lumen of 14 |
| 18 | orotracheal tube |
| 18' | infant orotracheal tube |
| 18a | air injection port of 18 |
| 18b | pilot tube of 18 |
| 19 | inflatable cuff of 18 |
| 20 | distal end of 18 |
| 20' | distal end of 18' |
| 22 | channel of guide element |
| 24 | plane between 12 and 14 |
| 26 | annulus portion of guide element |
| 28 | body portion of guide element |
| 30 | anterior wall of 22 |
| 30a | anterior arc portion of 26 |
| 32 | posterior wall of 22 |
| 32a | posterior arc portion of 26 |
| 34 | bearing surface extension of 32 |
| 36 | cusp |
| 38 | sidewalls of 22 |
| 40 | front wall of 12 |
| 42 | left outer wall of guide element |
| 44 | right outer wall of guide element |
| 46 | rear wall of guide element |
| 48 | occluding wall or tip of 28 |
| 50 | bottom undulating edge of 40 |
| 52 | edge of 42' 44 |
| 54 | left notch of 40 |
| 56 | right notch of 40 |
| 58 | central notch of 40 |
| 60 | mammillate nodule of 40 |
| 62 | mammillate nodule of 40 |
| 64 | recessed surface |
| 66 | edge of 34 |
| 70 | proximal end of 14 |
| 72 | forward end of 14 |
| 74 | outer wall of 14 |
| 75 | lumen wall of 14 |
| 76 | upper arcuate section of 74 |
| 77 | cutaway segment of 14 |
| 78 | lower arcuate section of 74 |
| 80 | exposed edge of 16 |
| 100 | mouth of 102 |
| 102 | patient |
| 104 | tongue of 102 |
| 106 | teeth of 102 |
| 108 | hump of 104 |
| 110 | posterior pharyngeal wall of 102 |
| 112 | throat of 102 |
| 114 | axis of 116 |
| 116 | trachea of 102 |
| 118 | larynx of 102 |
| 120 | opening of 118 |
| 122 | epiglottis of 102 |
| 124 | vallecular depression of 102 |
| 126 | vallecular depression of 102 |
| 128 | lumen of 118 |
| 130 | edge of 118 |
| 132 | interarytenoid incisure of 118 |
| 134 | opening of 136 |
| 136 | esophagus of 102 |
| 138 | median glosso-epiglottic fold of 102 |
| 140 | lateral glosso-epiglottic folds of 102 |
| 142 | pharyngo-epiglottic folds of 102 |
| 144 | airway path extension |
| 146 | connector tip of 18 |
| 147 | proximal end of 18 |
| 150 | esophageal tunnel |
| 152 | entrance hole to 150 |

TABLE I-continued

| Reference Number | Item |
|---|---|
| 154 | port to 150 |
| 156 | esophageal suction catheter |
| 160 | slant tunnel |
| 162 | entrance hole to 160 |
| 164 | port to 160 |
| 166 | vocal cords in 118 |
| 200 | fiberbundle of 222 or 224 |
| 222 | battery-powered laryngoscope |
| 224 | externally lit laryngoscope |
| 226 | distal end of 200 |
| 230 | laryngoscope support for 14 |
| 232 | circular band of 230 |
| 234 | handle of 222 |
| 236 | control body of 224 |
| 238 | front bolt bracket of 232 |
| 240 | front bolt bracket of 232 |
| 242 | rear bolt bracket of 232 |
| 244 | threaded bolt |
| 246 | central hole of 238 |
| 247 | central hole of 240 |
| 248 | wing nut |
| 250 | wing nut head of 244 |
| 252 | bolt bracket of 256 |
| 254 | bolt bracket of 256 |
| 256 | cradle of 230 |
| 258 | bolt |
| 260 | central hole of 252 |
| 262 | central hole of 242 |
| 264 | central hole of 254 |
| 266 | wing nut |
| 268 | U-shaped member of 256 |
| 270 | flat extension of 256 |
| 272 | flat extension of 256 |
| 274 | top edge of 268 |
| 276 | top edge of 268 |
| 278 | edges of 78 |
| 280 | body joining end of 200 |
| 282 | body of 222 |
| 286 | viewing eyepiece of 222 |
| 290 | eyepiece of 224 |
| 292 | external fiberbundle of 224 |
| 310 | second embodiment of a medical device |
| 312 | larynx of 314 |
| 314 | infant |
| 316 | epiglottis of 314 |
| 318 | opening of 312 |
| 320 | guide element of 310 |
| 322 | elliptical lower edge |
| 326 | posterior cartilage of 312 |
| 328 | front wall of 320 |
| 332 | inferior edge of 328 |
| 334 | base of 336 |
| 336 | anterior surface of 316 |
| 338 | tip of 316 |
| 340 | cutout |
| 342 | throat of 314 |
| 344 | mouth of 314 |
| 346 | tongue of 314 |
| 348 | posterior pharyngeal wall of 342 |
| 350 | third embodiment of a medical device |
| 352 | guide element of 350 |
| 354 | front wall of 352 |
| 356 | inferior edge of 34 |
| 358 | curved lower edge of 352 |
| 360 | posterior edge of 362 |
| 362 | posterior cartilage of 118 |
| 364 | lower anterior surface of 352 |
| 410 | fourth embodiment of a medical device |
| 412 | guide element of 410 |
| 450 | fifth embodiment of a medical device |
| 452 | guide element of 450 |
| 452' | modified guide element of 450 |
| 454 | curved blade handle member of 450 |
| 458 | blade-tube clip |
| 460 | slit in 26 |
| 462 | openable panel of 452 |
| 462' | openable panel of 452' |
| 464 | openable panel of 452 |
| 464' | openable panel of 452' |
| 466 | tack point |

TABLE I-continued

| Reference Number | Item |
|---|---|
| 468 | distal end of 454 |
| 480 | prongs of 468 |
| 482 | sockets in 452 |
| 482' | sockets in 498 |
| 484 | interference fit of 480' 482 |
| 486 | spring walls of 458 |
| 488 | base wall of 458 |
| 490 | tube-holding space of 458 |
| 492 | resilient flange of 458 |
| 494 | receiving slot of 458 |
| 496 | handle of 454 |
| 498 | modified front wall of 452 |
| 499 | modified rear wall of 452 |
| 500 | laryngoscope support |
| 502 | bite-protector clip |
| 504 | tubular port of 502 |
| 506 | rectangular port of 502 |
| 508 | slot of 502 |
| 510 | band of 500 |
| 512 | bolt bracket of 510 |
| 514 | bolt bracket of 510 |
| 516 | bolt bracket of 510 |
| 518 | bolt bracket of 510 |
| 520 | hole through 514 |
| 522 | head of 524 |
| 524 | bolt |
| 526 | hole through 512 |
| 528 | wing nut |
| 530 | hole through 516 |
| 532 | head of 534 |
| 534 | bolt |
| 536 | hole through 518 |
| 538 | wing nut |
| 540 | tongue member of 500 |
| 542 | hole through 542 |
| 544 | serrated edge of 516, 518, 540 |
| 546 | fillet of 500 |
| 548 | slot in 546 |
| 550 | head of 552 |
| 552 | bolt |
| 554 | hole in 454 |
| 556 | wing nut |

What is claimed is:

1. A method for blindly intubating a patient's trachea comprising:

inserting into the patient's throat an element having a tube guiding surface and an associated supporting edge, the element being sized to be received in the throat in the vicinity of the larynx and contoured to mate against reciprocal anatomical contours of and adjacent the larynx;

advancing the element into the throat until the reciprocal contours of the element and adjacent anatomy are mated together with the supporting edge of the tube guiding surface contiguous with at least the posterior edge of the larynx to effectively define an upward extension thereof such that the tube guiding surface is aimed into the larynx over the posterior edge thereof so that an intubation tube sliding along the tube guiding surface will be directed into the larynx and trachea; and advancing an intubation tube along the tube guiding surface and into the larynx and trachea.

2. A blind intubation guide comprising:

an element having a tube guiding surface with a supporting edge, the element being sized to be received in the throat in the vicinity of the larynx;

means associated with the element for situation the element in the throat with the supporting edge of the tube guiding surface contiguous with at least he posterior edge of the laryngeal opening to effectively define an upward extension thereof such that the tube guiding surface is aimed into the larynx over the posterior edge thereof so that an intubation tube sliding along the tube guiding surface will be directed into the larynx.

3. The intubation guide of claim 2 further comprising a handle extending from the element and sized to allow manipulation of the element in the throat from outside the mouth.

4. The intubation guide of claim 2 further comprising aperture means associated with the element for providing medical implement access aimed at the trachea when the element is situated in the throat with the supporting edge of the tube guiding surface contiguous with the posterior edge of the laryngeal opening.

5. The intubation guide of claim 2 wherein the tube guiding surface is arcuate.

6. The intubation guide of claim 2 further comprising recess means associated with the element adjacent the tube guiding surface for abutting the posterior wall of the larynx adjacent the laryngeal opening.

7. The intubation guide of claim 2 further comprising a member associated with the element and positioned to substantially surround the laryngeal opening when the element is situated in the throat with the supporting edge of the tube guiding surface contiguous with the posterior edge of the laryngeal opening.

8. The intubation guide of claim 2 further comprising means associated with the element for effectively blocking access between the esophagus and the larynx when the element is situated in the throat with the supporting edge of the tube guiding surface contiguous with the posterior edge of the laryngeal opening.

9. The intubation guide of claim 8 further comprising aperture means associated with the access blocking means for providing medical implement access to the esophagus when the element is situated in the throat with the supporting edge of the tube guiding surface contiguous with the posterior edge of the laryngeal opening.

10. The intubation guide of claim 2 further including means for aligning an intubation tube with the guiding surface to be guided therealong.

11. The intubation guide of claim 10 wherein the intubation tube guiding means includes a passageway through a portion of the element, the passageway being large enough for the intubation tube to pass therethrough.

12. The intubation guide of claim 10 further comprising a handle extending from the element and sized to allow manipulation of the element in the throat from outside the mouth, the intubation tube guiding means including a passageway through at least a portion of the handle, the passageway being large enough for the intubation tube to pass therethrough.

13. The intubation guide of claim 12 wherein the intubation tube guiding means further includes an extension of the passageway, the extension being through a portion of the element and being large enough for the intubation tube to pass therethrough.

14. A device for blindly inserting a tubular instrument through the mouth and into the larynx and trachea of a patient, the device comprising:

a channel having a proximal portion and a distal portion, the proximal portion including entrance access means for insertion of the tubular instrument into the channel, the distal portion including a cusplike distal tip with a convex supporting edge, the distal portion being curved downwardly relative the proximal portion such that when the device is inserted through the patient's mouth and into the throat, the distal portion extends into the patient's oropharynx and hypopharynx with the distal tip oriented toward the glottic opening inside the larynx and with the supporting edge positioned atop and contiguous with the posterior edge of the arlyngeal opening to effectively define an upward extension thereof.

15. The device of claim 14 wherein the proximal portion if longer than the distal portion such as to extend out of the patient's mouth and provide a handle for inserting the device into the throat.

16. The device of claim 14, the distal tip edge being U-shaped.

17. The device of claim 14, the distal tip edge being V-shaped.

18. The device of claim 14, further comprising tunnel means having a portion extending separately from, and adjacent to, the channel for communication with one of the esophagus and the larynx.

19. The device of claim 14 further comprising means for surrounding the epiglottis when the device is inserted into the throat.

20. The device of claim 19, the surrounding means including an aperture in the channel through which the epiglottis can pass.

* * * * *

UNITED STATES PATENT AND TRADEMARK OFFICE
CERTIFICATE OF CORRECTION

PATENT NO. : 5,339,805
DATED : August 23, 1994
INVENTOR(S) : Jeffrey D. Parker It is certified that error appears in the above-identified patent and that said Letters Patent is hereby corrected as shown below:

On title page, item [63] change the "Related U.S. Application Data" to read:

--Continuation of Ser. No. 879,873, May 7, 1992, Pat. No. 5,174,283, which is a continuation of PCT/US90/06351, Oct. 31, 1990, which is a continuation-in-part of Ser. No. 433,687, Nov. 8, 1989, Pat. No. 5,038,766.--

Column 22, line 2, "the illustrative" should read --and illustrative--.

Column 22, line 34 "42'" should read --42,--.

Column 24, line 9 "480'" should read --480,--.

Column 24, line 65 "situation" should read --situating--.

Column 24, line 67 "he" should read --the--.

Column 26, line 29 "arlyngeal" should read --laryngeal--.

Signed and Sealed this

Thirty-first Day of January, 1995

Attest:

BRUCE LEHMAN

*Attesting Officer*            *Commissioner of Patents and Trademarks*